(12) United States Patent
Inoue

(10) Patent No.: US 12,298,377 B2
(45) Date of Patent: May 13, 2025

(54) SIGNAL PROCESSING SYSTEM, SENSOR SYSTEM, SIGNAL PROCESSING METHOD, AND PROGRAM

(71) Applicant: Panasonic Intellectual Property Management Co., Ltd., Osaka (JP)

(72) Inventor: Kenichi Inoue, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 468 days.

(21) Appl. No.: 17/795,498

(22) PCT Filed: Jan. 7, 2021

(86) PCT No.: PCT/JP2021/000376
§ 371 (c)(1),
(2) Date: Jul. 26, 2022

(87) PCT Pub. No.: WO2021/153188
PCT Pub. Date: Aug. 5, 2021

(65) Prior Publication Data
US 2023/0108039 A1 Apr. 6, 2023

(30) Foreign Application Priority Data

Jan. 31, 2020 (JP) ................................ 2020-015862

(51) Int. Cl.
*G01S 13/04* (2006.01)
*A61B 5/05* (2021.01)
(Continued)

(52) U.S. Cl.
CPC .............. *G01S 13/04* (2013.01); *G01S 7/352* (2013.01); *G01S 7/412* (2013.01); *A61B 5/05* (2013.01)

(58) Field of Classification Search
CPC .......... G01S 13/04; G01S 7/352; G01S 7/412; A61B 5/05
See application file for complete search history.

(56) References Cited

U.S. PATENT DOCUMENTS 11,717,189 B2* 8/2023 Al-Alusi .............. A61B 5/7246
600/407
2008/0119716 A1* 5/2008 Boric-Lubecke .... A61B 5/7225
600/407
(Continued)

FOREIGN PATENT DOCUMENTS

JP 2014-083148 A 5/2014
JP 2015-068700 A 4/2015
(Continued)

OTHER PUBLICATIONS

English Translation of the Written Opinion of the International Searching Authority, International Patent Application No. PCT/JP2021/000376 (Year: 2021).*

(Continued)

*Primary Examiner* — Vladimir Magloire
*Assistant Examiner* — Noah Yi Min Zhu
(74) *Attorney, Agent, or Firm* — Rimon P.C.

(57) ABSTRACT

A signal processing system according to the present disclosure includes a difference calculation unit and a determination unit. The difference calculation unit uses a sensor signal at a reference timing and a plurality of the sensor signals at a plurality of comparative timings shifted from the reference timing. The difference calculation unit generates a plurality of differential signals as respective differences between the sensor signal at the reference timing and the plurality of the sensor signals at the plurality of comparative timings and obtains respective magnitudes of the plurality of differential signals as a plurality of differential values. The determination unit obtains an evaluation value based on the plurality (Continued)

of differential values and determines a property of the object by using the evaluation value.

17 Claims, 25 Drawing Sheets

(51) Int. Cl.
*G01S 7/35* (2006.01)
*G01S 7/41* (2006.01)

(56) References Cited

U.S. PATENT DOCUMENTS

| | | | |
|---|---|---|---|
| 2015/0309167 A1* | 10/2015 | Shikatani | G01S 13/18 342/27 |
| 2016/0100766 A1* | 4/2016 | Yoshioka | A61B 5/0082 600/301 |
| 2018/0055386 A1* | 3/2018 | Zielinski | A61B 5/08 |
| 2018/0235506 A1* | 8/2018 | Cho | A61B 5/0507 |
| 2019/0069810 A1* | 3/2019 | Suematsu | A61B 5/11 |
| 2019/0383928 A1* | 12/2019 | Kuwahara | G01S 13/343 |
| 2020/0367765 A1* | 11/2020 | Bacher | G01R 33/56308 |
| 2023/0112537 A1* | 4/2023 | Sakamoto | A61B 5/7264 342/22 |

FOREIGN PATENT DOCUMENTS

| | | |
|---|---|---|
| JP | 2015-096831 A | 5/2015 |
| WO | 2017/149923 A1 | 9/2017 |
| WO | 2018/220701 A1 | 12/2018 |

OTHER PUBLICATIONS

International Search Report dated Feb. 22, 2021 issued in International Patent Application No. PCT/JP2021/000376, with English translation.

Sekine, Masatoshi et al., Human Detection Algorithm for Doppler Radar Using Prediction Error in Autoregressive Model, 2012 8th IEEE International Symposium on Instrumentation and Control Technology (ISICT), 2012.07, DOI: 10.1109/ISICT.2012.6291657.

* cited by examiner

SIGNAL PROCESSING SYSTEM, SENSOR SYSTEM, SIGNAL PROCESSING METHOD, AND PROGRAM

CROSS-REFERENCE OF RELATED APPLICATIONS

This application is the U.S. National Phase under 35 U.S.C. § 371 of International Patent Application No. PCT/JP2021/000376, filed on Jan. 7, 2021, which in turn claims the benefit of Japanese Patent Application No. 2020-015862, filed on Jan. 31, 2020, the entire disclosures of which Applications are incorporated by reference herein.

TECHNICAL FIELD

The present disclosure relates to a signal processing system, a sensor system, a signal processing method, and a program.

BACKGROUND ART

Patent Literature 1 discloses a body motion signal processing device for sensing, based on a reflected wave, the condition of a person who is taking a bath in a bathroom. The reflected wave is obtained by irradiating the bathroom with a microwave (radio wave).

The body motion signal processing device transmits a radio wave inside the bathroom, receives, as a reception signal, the radio wave reflected inside the bathroom, and detects a body motion signal, representing the motion of the subject's body, based on the reception signal. Then, the body motion signal processing device compares the amplitude value of a signal corresponding to a body motion region component and included in the reception signal detected when the subject (i.e., the person who is going to take a bath) is absent from the bathroom with the amplitude value of the body motion signal detected when the subject is taking a bath there, thereby detecting the body motion (represented by his or her heart rate and respiration, for example) of the subject in the bathroom. In addition, the body motion signal processing device sends, as needed, a notification as an alert depending on the subject's condition.

A signal processing system such as the body motion signal processing device described above is required to determine the property of an object such as a person more accurately.

CITATION LIST

Patent Literature

Patent Literature 1: WO 2017/149923A1

SUMMARY OF INVENTION

An object of the present disclosure is to provide a signal processing system, a sensor system, a signal processing method, and a program, all of which are configured or designed to determine the property of an object accurately.

A signal processing system according to an aspect of the present disclosure receives, from a radio wave sensor which sends out a radio wave as a transmission wave and which receives, as a reception wave, the radio wave reflected from an object, a sensor signal including information about a distance between the radio wave sensor and the object. The signal processing system includes a difference calculation unit and a determination unit. The difference calculation unit uses the sensor signal at a reference timing and a plurality of the sensor signals at a plurality of comparative timings shifted from the reference timing. The difference calculation unit generates a plurality of differential signals as respective differences between the sensor signal at the reference timing and the plurality of the sensor signals at the plurality of comparative timings and obtains respective magnitudes of the plurality of differential signals as a plurality of differential values. The determination unit obtains an evaluation value based on the plurality of differential values and determines a property of the object by using the evaluation value.

A sensor system according to another aspect of the present disclosure includes the signal processing system described above and the radio wave sensor.

A signal processing method according to still another aspect of the present disclosure includes receiving, from a radio wave sensor which sends out a radio wave as a transmission wave and which receives, as a reception wave, the radio wave reflected from an object, a sensor signal including information about a distance between the radio wave sensor and the object. The signal processing method includes a difference calculation step and a determination step. The difference calculation step includes using the sensor signal at a reference timing and a plurality of the sensor signals at a plurality of comparative timings shifted from the reference timing. The difference calculation step includes generating a plurality of differential signals as respective differences between the sensor signal at the reference timing and the plurality of the sensor signals at the plurality of comparative timings and obtaining respective magnitudes of the plurality of differential signals as a plurality of differential values. The determination step includes obtaining an evaluation value based on the plurality of differential values and determining a property of the object by using the evaluation value.

A program according to yet another aspect of the present disclosure is designed to cause a computer system to perform the signal processing method described above.

DESCRIPTION OF EMBODIMENTS

The present disclosure generally relates to a signal processing system, a sensor system, a signal processing method, and a program. More particularly, the present disclosure relates to a signal processing system, a sensor system, a signal processing method, and a program, all of which are configured or designed to determine an object's property by using a radio wave sensor.

Note that the embodiments to be described below and their variations are only exemplary ones of various embodiments and variations of the present disclosure and should not be construed as limiting. Rather, those exemplary embodiments and variations may be readily modified in various manners depending on a design choice or any other factor without departing from a true spirit and scope of the present disclosure.

(1) First Embodiment (1.1) Overview of Sensor System

Figure 1:
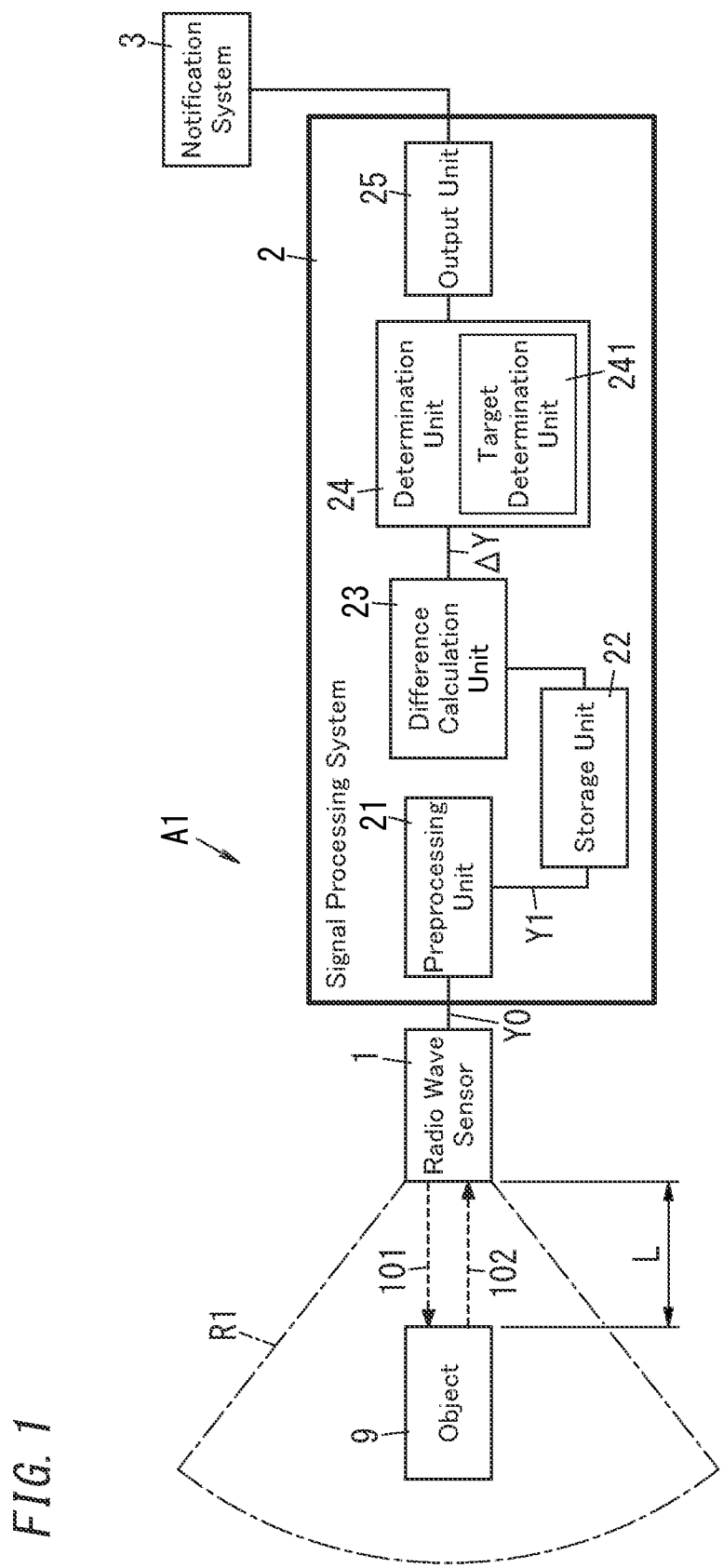
FIG. 1 is a block diagram illustrating a sensor system including a signal processing system according to a first embodiment.

FIG. 1 illustrates a sensor system A1 including a signal processing system 2 according to a first embodiment.

The sensor system A1 includes a radio wave sensor 1 and the signal processing system 2. The signal processing system 2 according to this embodiment is implemented as a signal processor.

The radio wave sensor 1 sends out a radio wave as a transmission wave 101 within an irradiation area R1, receives, as a reception wave 102, the radio wave reflected from an object 9 within the irradiation area R1, and outputs a sensor signal Y0 including information about the distance L between the radio wave sensor 1 and the object 9.

The signal processing system 2 determines a property of the object 9 by performing signal processing on the sensor signal Y0 supplied from the radio wave sensor 1.

The distance L to the object 9 varies due to not only the movement of the object 9 but also motion of only a part of the object 9. For example, if the object 9 is a person, subjecting the sensor signal Y0 including information about the distance L to signal processing enables deriving information about the motion of the person including not only information about his or her movement but also biometric information such as his or her respiratory rate, heart rate, and pulse. That is to say, if the object 9 is a person, examples of the properties of the object 9 include the presence of the person, his or her motion velocity, his or her location, and biometric information.

(1.2) Radio Wave Sensor

Figure 2:
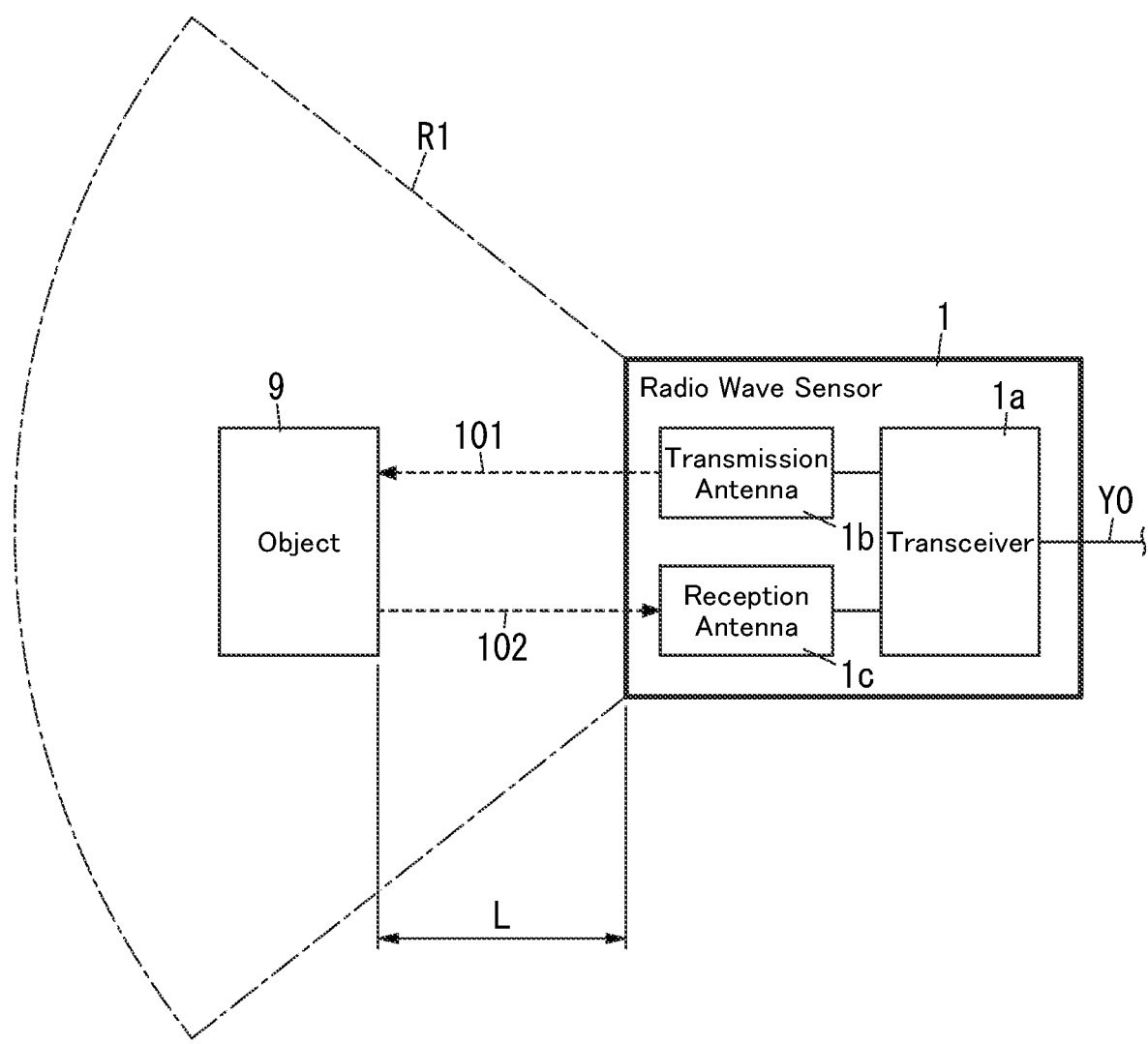
FIG. 2 is a block diagram illustrating a radio wave sensor according to the first embodiment.

The radio wave sensor 1 according to this embodiment is a frequency-modulated continuous-wave (FMCW) radio wave sensor. As shown in FIG. 2, the radio wave sensor 1 includes a transceiver 1a, a transmission antenna 1b, and a reception antenna 1c. The transceiver 1a sends out, via the transmission antenna 1b, a transmission wave 101, of which the frequency (transmission frequency) varies with the passage of time, and receives, via the reception antenna 1c, a reception wave 102, of which the frequency (reception frequency) varies with the passage of time. Then, the transceiver 1a generates, as a sensor signal Y0, a beat signal, of which the frequency (beat frequency) is equal to the frequency difference between the transmission frequency and the reception frequency. The signal processing system 2 receives the sensor signal Y0 from the radio wave sensor 1 and may determine the distance to the object 9 based on the beat frequency of the sensor signal Y0. Note that the transmission wave 101 is preferably a microwave. In particular, the transmission wave 101 preferably has a frequency of 24.15 GHz. However, the transmission wave 101 does not have to be a microwave but may also be a millimeter wave and the frequency of the transmission wave 101 is not limited to any particular value.

Specifically, the transceiver 1a that adopts the FMCW method repeatedly performs sweep processing in which the frequency of the transmission wave 101 (i.e., the transmission frequency) is alternately increased and then decreased a number of times. According to the sweep processing, the transmission frequency is increased by a sweep frequency width Δfa during a sweep time Ta. The transceiver 1a receives the reflected wave in a time 2L/C, where C is the speed of light, after the transmission wave 101 has been sent out. The frequency of the reflected wave (i.e., the reception frequency), as well as the transmission frequency, also varies with the passage of time. Then, the transceiver 1a generates a beat signal, of which the frequency (beat frequency) fb is equal to the frequency difference between the transmission frequency and the reception frequency, and outputs the beat signal as the sensor signal Y0. The beat frequency fb is given by fb=[(Δfa·2L)/(C·Ta)]. Thus, the distance L to the object 9 is expressed by the following Equation (1):

$$L=(fb \cdot C \cdot Ta)/(2 \cdot \Delta fa) \tag{1}$$

Then, the radio wave sensor 1 outputs, as the sensor signal Y0 (i.e., a beat signal having a frequency fb), an IQ signal including an in-phase component and a quadrature component. In the following description, the in-phase component will be hereinafter sometimes referred to as an "I component" and the quadrature component will be hereinafter sometimes referred to as a "Q component."

(1.3) Signal Processing System (Signal Processor)

(1.3.1) Overview of Signal Processing System

As shown in FIG. 1, the signal processing system 2 includes a preprocessing unit 21, a storage unit 22, a difference calculation unit 23, a determination unit 24, and an output unit 25.

The preprocessing unit 21 has an amplification function of amplifying the sensor signal Y0 and an AD conversion function of converting the sensor signal Y0 into a digital signal. The preprocessing unit 21 stores a digital sensor signal Y1 thus amplified in the storage unit 22. The sensor signal Y1 is a signal obtained by subjecting the sensor signal Y0 to amplification processing and AD conversion processing and is substantially the same signal as the sensor signal Y0. Thus, each of the sensor signal Y0 and the sensor signal Y1 may be regarded as a sensor signal including information about the distance L to the object 9. Alternatively, the radio wave sensor 1 may include the preprocessing unit 21. In that case, the sensor signal Y1 supplied from the radio wave sensor 1 is stored in the storage unit 22.

The storage unit 22 stores the history of the sensor signals Y1. That is to say, the storage unit 22 time-sequentially stores a plurality of sensor signals Y1 generated by the preprocessing unit 21. The history of the sensor signals Y1 represents the variation of the sensor signals Y1 during a predetermined period in the past.

The difference calculation unit 23 generates a plurality of differential signals ΔY based on the history of the sensor signals Y1 as stored in the storage unit 22 and obtains the respective magnitudes of the plurality of differential signals ΔY as a plurality of differential values ΔZ. The difference calculation unit 23 will be described in detail later.

The determination unit 24 obtains an evaluation value based on the plurality of differential values ΔZ and determines a property of the object 9 by using the evaluation value. Examples of the properties of the object 9 include the type of the object 9, the presence or absence of the object 9, and its motion velocity, location, and motion. The determination unit 24 will be described in further detail later.

The output unit 25 outputs the decision made by the determination unit 24 to a notification system 3. Communication between the output unit 25 and the notification system 3 is established by either wired communication via a communications line or wireless communication using a wireless signal. The wired communication may be established via a twisted pair of cables, a dedicated communications line, or a LAN (local area network) cable, for example. The wireless communication may be either a wireless communication compliant with a standard such as Wi-Fi®, Bluetooth®, ZigBee®, or a low power radio standard requiring no license (e.g., Specified Low Power Radio) or a wireless communication such as infrared communication.

The signal processing system 2 described above preferably includes a computer system. The computer system may include a processor and a memory as principal hardware components thereof. At least some functions of the signal processing system 2 according to the present disclosure may be performed by making the processor execute a program stored in the memory of the computer system. The program may be stored in advance in the memory of the computer system. Alternatively, the program may also be downloaded through a telecommunications line or be distributed after having been recorded in some non-transitory storage medium such as a memory card, an optical disc, or a hard disk drive, any of which is readable for the computer system. The processor of the computer system may be implemented as a single or a plurality of electronic circuits including a semiconductor integrated circuit (IC) or a large-scale integrated circuit (LSI). As used herein, the "integrated circuit" such as an IC or an LSI is called by a different name depending on the degree of integration thereof. Examples of the integrated circuits include a system LSI, a very-large-scale integrated circuit (VLSI), and an ultra-large-scale integrated circuit (ULSI). Optionally, a field-programmable gate array (FPGA) to be programmed after an LSI has been fabricated or a reconfigurable logic device allowing the connections or circuit sections inside of an LSI to be reconfigured may also be adopted as the processor. Those electronic circuits may be either integrated together on a single chip or distributed on multiple chips, whichever is appropriate. Those multiple chips may be aggregated together in a single device or distributed in multiple devices without limitation. As used herein, the "computer system" includes a microcontroller including one or more processors and one or more memories. Thus, the microcontroller may also be implemented as a single or a plurality of electronic circuits including a semiconductor integrated circuit or a large-scale integrated circuit.

Also, the computer system may also be a system made up of either a single computer or a plurality of computers. For example, at least some functions of the preprocessing unit 21, the storage unit 22, the difference calculation unit 23, the determination unit 24, and the output unit 25 may also be implemented as a cloud computing system.

The notification system 3 includes at least one of a server, a personal computer, a dedicated terminal, a smartphone, or a tablet computer, and performs a notification operation or an alert operation based on the decision made by the determination unit 24.

(1.3.2) Signal Processing

In this embodiment, the signal processing system 2 includes the difference calculation unit 23 and the determination unit 24 and determines, as a property of the object 9 within the irradiation area R1, whether or not the object 9 is a person.

The radio wave sensor 1 is provided in a room and sends out the transmission wave 101 toward the irradiation area R1 in the room. In the room, arranged are electric appliances (such as an electric fan and a robotic vacuum cleaner) as exemplary objects 9 and movable equipment such as curtains. In addition, a person as an exemplary object 9 enters and leaves the irradiation area R1. In that case, for the signal processing system 2, the person is the target of detection, and the movable equipment is the disturbance object other than the target of detection.

(Difference Calculation Unit)

The difference calculation unit 23 generates a plurality of differential signals ΔY and obtains the respective magnitudes of the plurality of differential signals ΔY as a plurality of differential values ΔZ. Each of the differential signals ΔY is a differential signal between a pair of sensor signals Y1 at two different timings and is a signal from which a signal component caused by a still object 9, a signal component caused by background noise, and other signal components are removed.

Figure 3:
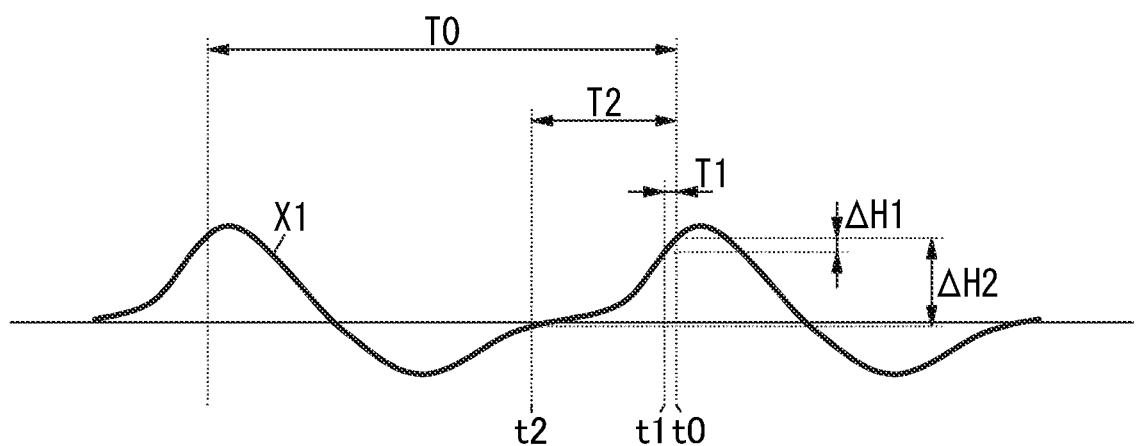
FIG. 3 is a waveform diagram showing a phase difference between I and Q components of a sensor signal in the first embodiment.

If the object 9 is a person, then the motion of the person caused by his or her respiration varies the respective magnitudes of the I and Q components of the sensor signal Y1 (or Y0) and the phase difference between the I and Q components. FIG. 3 shows the waveform X1 of the phase difference between the I and Q components of the sensor signal Y1. As shown in FIG. 3, the waveform X1 pulsates in a respiratory cycle T0. In FIG. 3, shown are a reference timing t0, a first comparative timing t1 which is the previous timing with respect to the reference timing t0, and a second comparative timing t2 which is earlier than the first comparative timing t1. The second comparative timing t2 is a timing earlier than the reference timing t0 by a time length that is equal to or greater than a quarter of one respiratory cycle T0 and equal to or less than a half of one respiratory cycle T0. That is to say, the time length of a period T2 between the reference timing t0 and the second comparative timing t2 is greater than the time length of a period T1 between the reference timing t0 and the first comparative timing t1. In addition, the width $\Delta H2$ of the variation (hereinafter referred to as "variation width $\Delta H2$") in the waveform X1 during the period T2 shown in FIG. 3 is greater than the width $\Delta H1$ of the variation (hereinafter referred to as "variation width $\Delta H1$") in the waveform X1 during the period T1 shown in FIG. 3. The variation width $\Delta H1$ is obtained by subtracting the magnitude of the waveform X1 at the first comparative timing t1 from the magnitude of the waveform X1 at the reference timing t0. The variation width $\Delta H2$ is obtained by subtracting the magnitude of the waveform X1 at the second comparative timing t2 from the magnitude of the waveform X1 at the reference timing t0.

That is to say, supposing the sensor signal Y1 at a timing to is designated by Y1($tn$), if the object 9 is a person, then the difference between the sensor signal Y1($t0$) and the sensor signal Y1($t2$) tends to be greater than the difference between the sensor signal Y1($t0$) and the sensor signal Y1($t1$).

Thus, the differential signal $\Delta Y$ between the sensor signal Y1($t0$) and the sensor signal Y1($t1$) will be hereinafter referred to as a "first differential signal $\Delta Y(t0, t1)$" and the differential signal $\Delta Y$ between the sensor signal Y1($t0$) and the sensor signal Y1($t2$) will be hereinafter referred to as a "second differential signal $\Delta Y(t0, t2)$." The first differential signal $\Delta Y(t0, t1)$ is given by [Y1($t0$)-Y1($t1$)]. The second differential signal $\Delta Y(t0, t2)$ is given by [Y1($t0$)-Y1($t2$)].

Optionally, the difference calculation unit 23 may generate the differential signal $\Delta Y$ in a frequency domain by subjecting the differential signal $\Delta Y$ in a time domain to either fast Fourier transform (FFT) or discrete cosine transform (DCT). In that case, the first differential signal $\Delta Y(t0, t1)$ will be a signal in the frequency domain which is generated by subjecting [Y1($t0$)-Y1($t1$)] to either FFT or DCT. The second differential signal $\Delta Y(t0, t2)$ will be a signal in the frequency domain which is generated by subjecting [Y1($t0$)-Y1($t2$)] to either FFT or DCT. The first differential signal $\Delta Y(t0, t1)$ and second differential signal $\Delta Y(t0, t2)$ in the frequency domain are each expressed by a complex number.

Furthermore, the difference calculation unit 23 may divide the entire frequency range in the frequency domain into a plurality of frequency bins and may use a signal component in either a particular frequency bin or particular frequency bins as the differential signal $\Delta Y$. Using the signal component in the particular frequency bin(s) as the differential signal $\Delta Y$ allows the determination unit 24 to determine a property of the object 9 by paying attention to only the object 9 present at a particular distance L or within a particular distance L range.

Figure 4A:
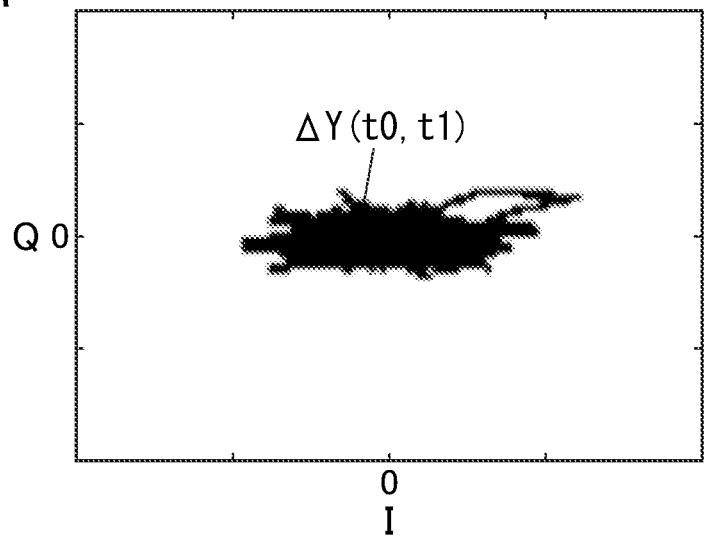
FIG. 4A shows the trajectory of a first differential signal in an IQ plane according to the first embodiment.
Figure 4B:
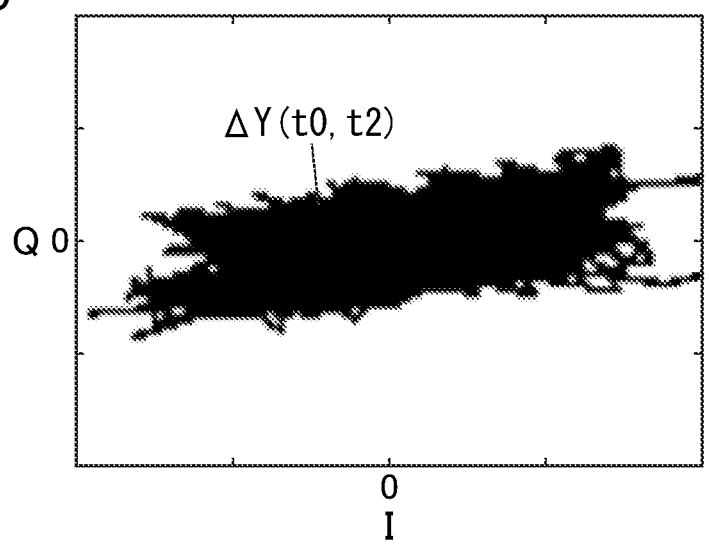
FIG. 4B shows the trajectory of a second differential signal in the IQ plane.

The difference calculation unit 23 obtains the first differential signal $\Delta Y(t0, t1)$ and second differential signal $\Delta Y(t0, t2)$ in every regular computational cycle (which is a cycle sufficiently shorter than one respiratory cycle T0). FIG. 4A shows, on an IQ plane, the trajectory of the first differential signal $\Delta Y(t0, t1)$ obtained in every computational cycle in a situation where the object 9 is a person who is sleeping in bed (hereinafter referred to as a "sleeping person"). FIG. 4B shows, on an IQ plane, the trajectory of the second differential signal $\Delta Y(t0, t2)$ obtained in every computational cycle in a situation where the object 9 is a sleeping person. The first differential signal $\Delta Y(t0, t1)$ and the second differential signal $\Delta Y(t0, t2)$ change around a point where I=0 and Q=0, and the trajectory of the second differential signal $\Delta Y(t0, t2)$ is distributed in a broader range than the trajectory of the first differential signal $\Delta Y(t0, t1)$. Then, the difference calculation unit 23 obtains, as the first differential value $\Delta Z1$, the average per predetermined time (i.e., time average) of the magnitudes of the first differential signal $\Delta Y(t0, t1)$. In addition, the difference calculation unit 23 also obtains, as the second differential value $\Delta Z2$, the average per predetermined time (i.e., time average) of the magnitudes of the second differential signal $\Delta Y(t0, t2)$. In that case, the second differential value $\Delta Z2$ becomes significantly larger than the first differential value $\Delta Z1$. In this example, the time length of the period T1 is supposed to be 50 msec and the time length of the period T2 is supposed to be 500 msec.

Furthermore, the magnitude of the first differential signal $\Delta Y(t0, t1)$ is the respective magnitudes of the I and Q components of the first differential signal $\Delta Y(t0, t1)$, the magnitude of only the I component of the first differential signal $\Delta Y(t0, t1)$, or the magnitude of only the Q component of the first differential signal $\Delta Y(t0, t1)$. Likewise, the magnitude of the second differential signal $\Delta Y(t0, t2)$ is the respective magnitudes of the I and Q components of the second differential signal $\Delta Y(t0, t2)$, the magnitude of only the I component of the second differential signal $\Delta Y(t0, t2)$, or the magnitude of only the Q component of the second differential signal $\Delta Y(t0, t2)$.

Note that if the respiratory rate of a sleeping person is going to be detected, then the period T2 is preferably set at a value falling within the range from 500 msec to 7 sec. On the other hand, if the respiratory rate of a person 91 who is awake is going to be detected, then the periods T1, T2 are set to have shorter time lengths. Nevertheless, the respective time lengths of the periods T1, T2 are preferably set according to, for example, the person who is the target of detection or the movement of the person who is the target of detection.

Figure 5A:
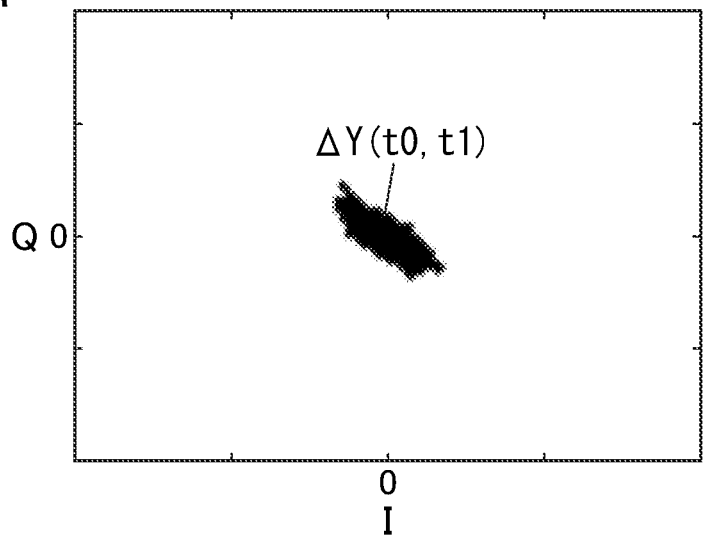
FIG. 5A shows the trajectory of another first differential signal in the IQ plane according to the first embodiment.
Figure 5B:
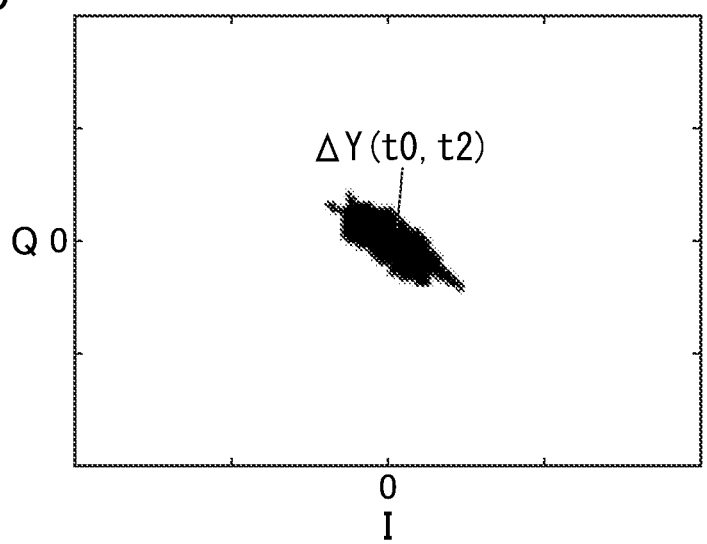
FIG. 5B shows the trajectory of another second differential signal in the IQ plane.

On the other hand, if the object 9 is a curtain, then the trajectory of the first differential signal $\Delta Y(t0, t1)$ and the trajectory of the second differential signal $\Delta Y(t0, t2)$ are distributed in substantially the same ranges as shown in FIGS. 5A and 5B. As a result, the first differential value $\Delta Z1$ and the second differential value $\Delta Z2$ are approximately equal to each other.

Figure 6A:
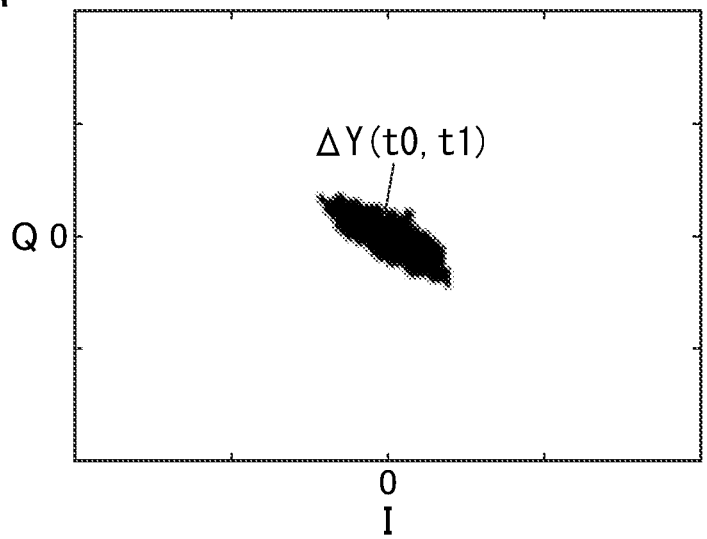
FIG. 6A shows the trajectory of still another first differential signal in the IQ plane according to the first embodiment.
Figure 6B:
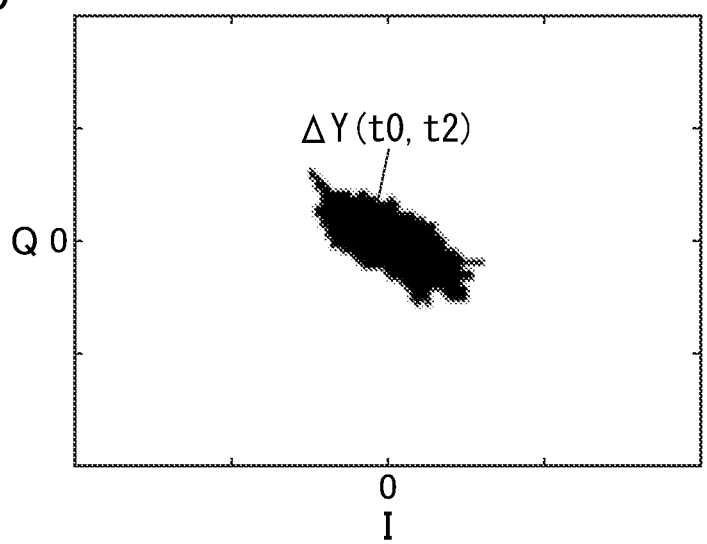
FIG. 6B shows the trajectory of still another second differential signal in the IQ plane.

Furthermore, if the object 9 is an electric fan that is swinging, then the trajectory of the second differential signal $\Delta Y(t0, t2)$ is distributed in a slightly broader range than the trajectory of the first differential signal $\Delta Y(t0, t1)$ as shown in FIGS. 6A and 6B. As a result, the second differential value $\Delta Z2$ becomes slightly larger than the first differential value $\Delta Z1$.

Figure 7A:
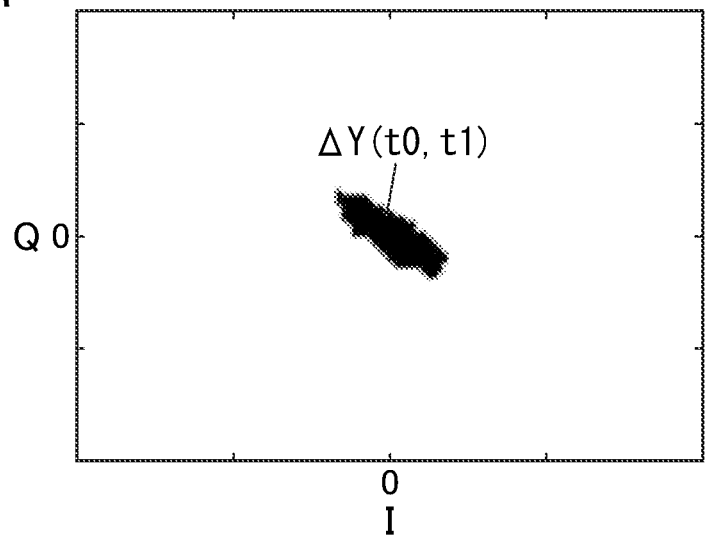
FIG. 7A shows the trajectory of yet another first differential signal in the IQ plane according to the first embodiment.
Figure 7B:
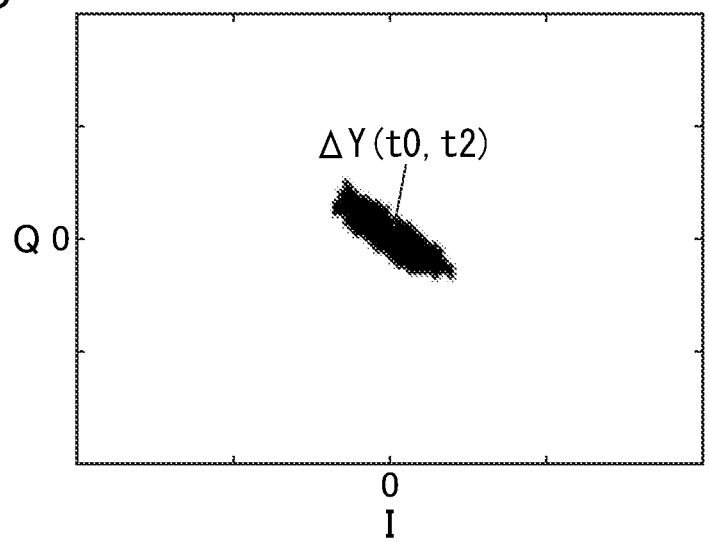
FIG. 7B shows the trajectory of yet another second differential signal in the IQ plane.

On the other hand, if the object 9 is an electric fan that is not swinging, then the trajectory of the first differential signal $\Delta Y(t0, t1)$ and the trajectory of the second differential signal $\Delta Y(t0, t2)$ are distributed in substantially the same ranges as shown in FIGS. 7A and 7B. As a result, the first differential value $\Delta Z1$ and the second differential value $\Delta Z2$ are approximately equal to each other.

Optionally, the difference calculation unit 23 may obtain, as the first differential value $\Delta Z1$, the effective value (i.e., the root mean square (RMS)) of the magnitudes of the first differential signal $\Delta Y(t0, t1)$ and obtain, as the second differential value $\Delta Z2$, the RMS of the magnitudes of the second differential signal $\Delta Y(t0, t2)$. Alternatively, the difference calculation unit 23 may obtain, as the first differential value $\Delta Z1$, the standard deviation of the magnitudes of the first differential signal $\Delta Y(t0, t1)$ and obtain, as the second differential value $\Delta Z2$, the standard deviation of the magnitudes of the second differential signal $\Delta Y(t0, t2)$. Still alternatively, the difference calculation unit 23 may also obtain the first differential value $\Delta Z1$ and the second differential value $\Delta Z2$ after having passed the time function of the first differential signal $\Delta Y(t0, t1)$ and the second differential signal $\Delta Y(t0, t2)$ through a filter such as a low-pass filter.

(Determination Unit)

The determination unit 24 includes a target determination unit 241.

The target determination unit 241 obtains an evaluation value Ga based on the first differential value $\Delta Z1$ and the second differential value $\Delta Z2$ and determines a property of the object 9 by using the evaluation value Ga. In this embodiment, the target determination unit 241 determines, as the property of the object 9, whether or not the object 9 is a person.

The target determination unit 241 preferably obtains the evaluation value Ga by using the $[\Delta Z2/\Delta Z1]$ ratio of the second differential value $\Delta Z2$ to the first differential value $\Delta Z1$. Using the $[\Delta Z2/\Delta Z1]$ ratio makes the evaluation value Ga a relative value (i.e., a standardized value), thus contributing to improving the accuracy of the determination processing.

For example, the target determination unit 241 obtains, as the evaluation value Ga, an evaluation value Ga1 by the following Equation (2). The evaluation value Ga1 obtained by Equation (2) becomes greater than one if the object 9 is a person but becomes approximately equal to one if the object 9 is a disturbance object such as a curtain or an electric fan.

$$Ga1 = \Delta Z2/\Delta Z1 \tag{2}$$

Alternatively, the target determination unit 241 obtains, as the evaluation value Ga, an evaluation value Ga2 by the following Equation (3). The evaluation value Ga2 obtained by Equation (3) approaches one if the object 9 is a person and approaches zero if the object 9 is a disturbance object such as a curtain or an electric fan.

$$Ga2 = 1 - \Delta Z1/\Delta Z2 \tag{3}$$

FIGS. 8A and 8B, FIGS. 9A and 9B, FIGS. 10A and 10B, FIGS. 11A and 11B, and FIGS. 12A and 12B each show how the evaluation value Ga2 changes with time. The evaluation value Ga2 shown in each of FIGS. 8A, 9A, 10A, 11A, and 12A is obtained based on the first differential value $\Delta Z1$ that is the RMS of the magnitudes of the first differential signal $\Delta Y(t0, t1)$ and the second differential value $\Delta Z2$ that is the RMS of the magnitudes of the second differential signal $\Delta Y(t0, t2)$. On the other hand, the evaluation value Ga2 shown in each of FIGS. 8B, 9B, 10B, 11B, and 12B is obtained based on the first differential value $\Delta Z1$ that is the standard deviation of the magnitudes of the first differential signal $\Delta Y(t0, t1)$ and the second differential value $\Delta Z2$ that is the standard deviation of the magnitudes of the second differential signal $\Delta Y(t0, t2)$.

Furthermore, Ka1 and Ka2 shown in each of FIGS. 8A and 8B, FIGS. 9A and 9B, FIGS. 10A and 10B, FIGS. 11A and 11B, and FIGS. 12A and 12B are evaluation threshold values to be compared with an associated evaluation value Ga2. In this embodiment, the evaluation threshold value Ka1 is set at 0.5 and the evaluation threshold value Ka2 is set at 0.1.

Figure 8A:
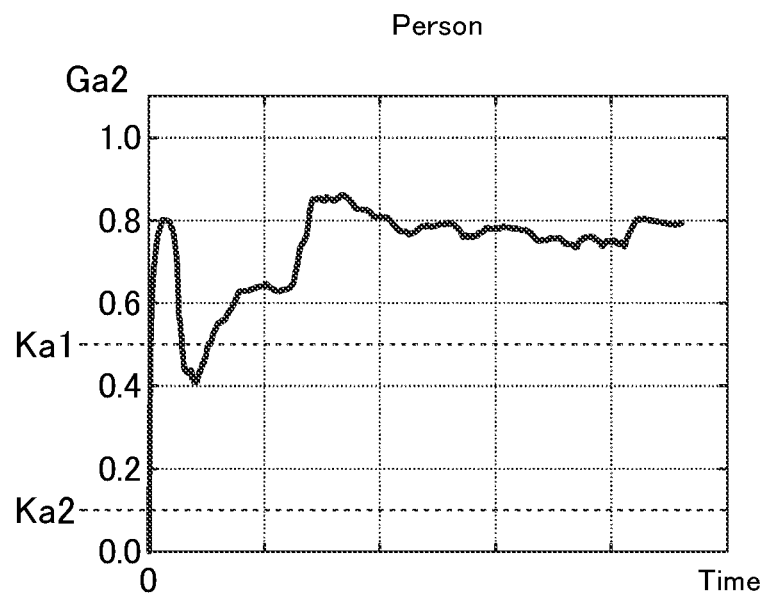
FIGS. 8A and 8B each show how an evaluation value changes with time in the first embodiment.
Figure 8B:
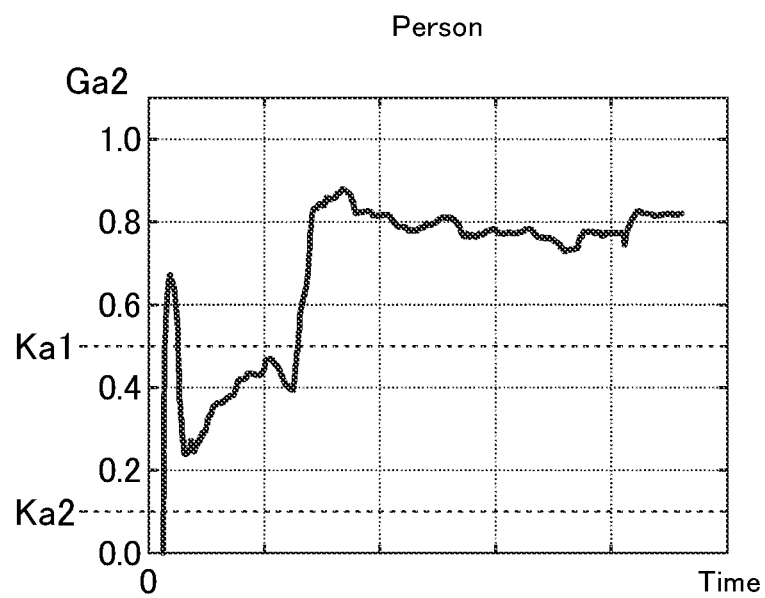

FIGS. 8A and 8B show how the evaluation value Ga2 changes with time in a situation where the object 9 is a person who is seated still. In FIGS. 8A and 8B, the evaluation value Ga2 approaches one and the evaluation value Ga2 remains equal to or greater than the evaluation threshold value Ka1 for a longer period of time.

Figure 9A:
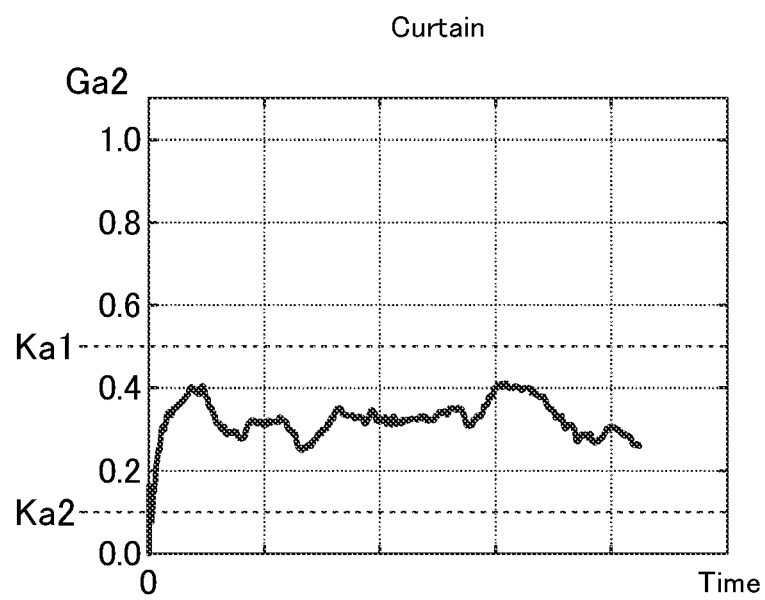
FIGS. 9A and 9B each show how an evaluation value changes with time in the first embodiment.
Figure 9B:
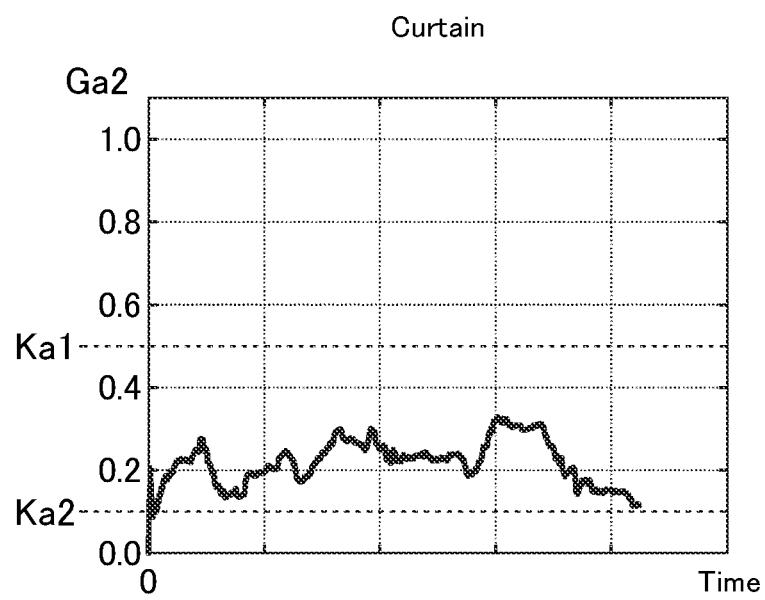

FIGS. 9A and 9B show how the evaluation value Ga2 changes with time in a situation where the object 9 is a curtain. In that case, the flutter of the curtain in wind, for example, causes the evaluation value Ga2 to increase more easily. However, one cycle in which the curtain flutters is different from one respiratory cycle T0 of the person. Thus, setting the respective time lengths of the periods T1, T2 at respective values corresponding to one respiratory cycle T0 of the person (see FIG. 3) may reduce an excessive increase in the evaluation value Ga2 in a situation where the object 9 is a curtain. In FIGS. 9A and 9B, the evaluation value Ga2 remains less than the evaluation threshold value Ka1 and equal to or greater than the evaluation threshold value Ka2 for a longer period of time.

Figure 10A:
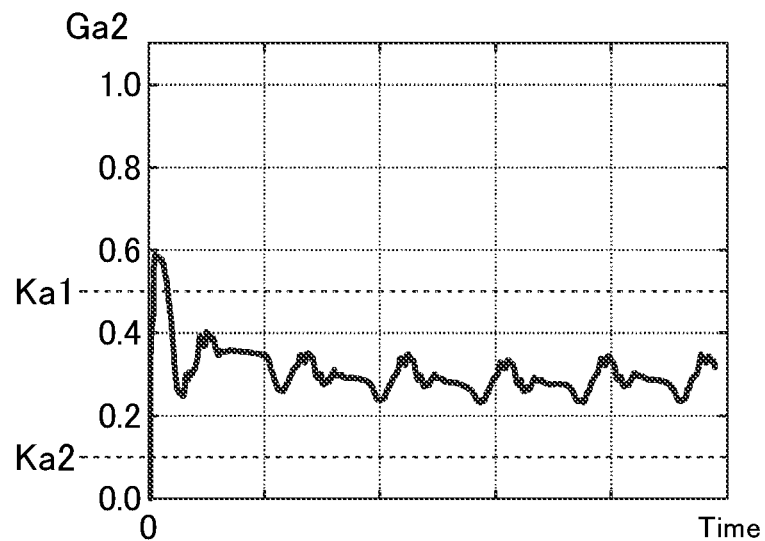
FIGS. 10A and 10B each show how an evaluation value changes with time in the first embodiment.
Figure 10B:
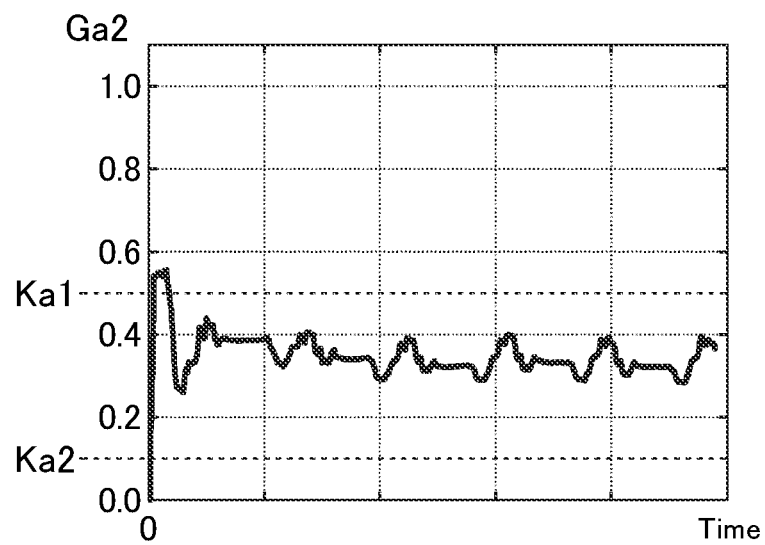

FIGS. 10A and 10B show how the evaluation value Ga2 changes with time in a situation where the object 9 is an electric fan that is swinging. In that case, the swing of the electric fan causes the evaluation value Ga2 to increase more easily. However, one cycle in which the electric fan swings is different from one respiratory cycle T0 of the person. Thus, setting the respective time lengths of the periods T1, T2 at respective values corresponding to one respiratory cycle T0 of the person (see FIG. 3) may reduce an excessive increase in the evaluation value Ga2 in a situation where the object 9 is an electric fan that is swinging. In FIGS. 10A and 10B, the evaluation value Ga2 remains less than the evaluation threshold value Ka1 and equal to or greater than the evaluation threshold value Ka2 for a longer period of time.

Figure 11A:
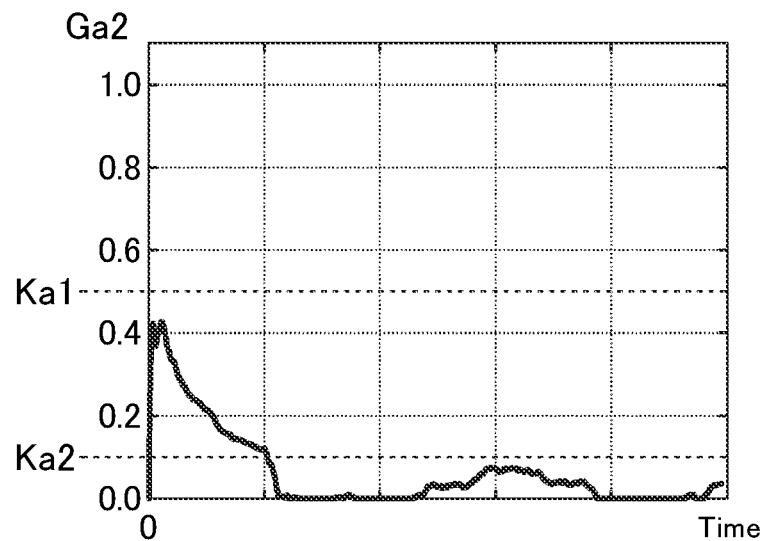
FIGS. 11A and 11B each show how an evaluation value changes with time in the first embodiment.
Figure 11B:
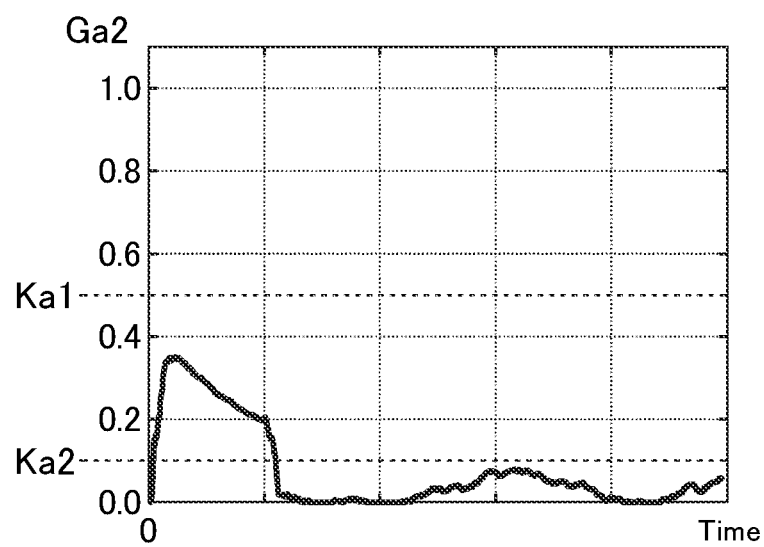

FIGS. 11A and 11B show how the evaluation value Ga2 changes with time in a situation where the object 9 is an electric fan that is not swinging (i.e., fixed). In that case, no swing of the electric fan makes the evaluation value Ga2 smaller than in FIGS. 10A and 10B. In FIGS. 11A and 11B, the evaluation value Ga2 remains less than the evaluation threshold value Ka2 for a longer period of time.

Figure 12A:
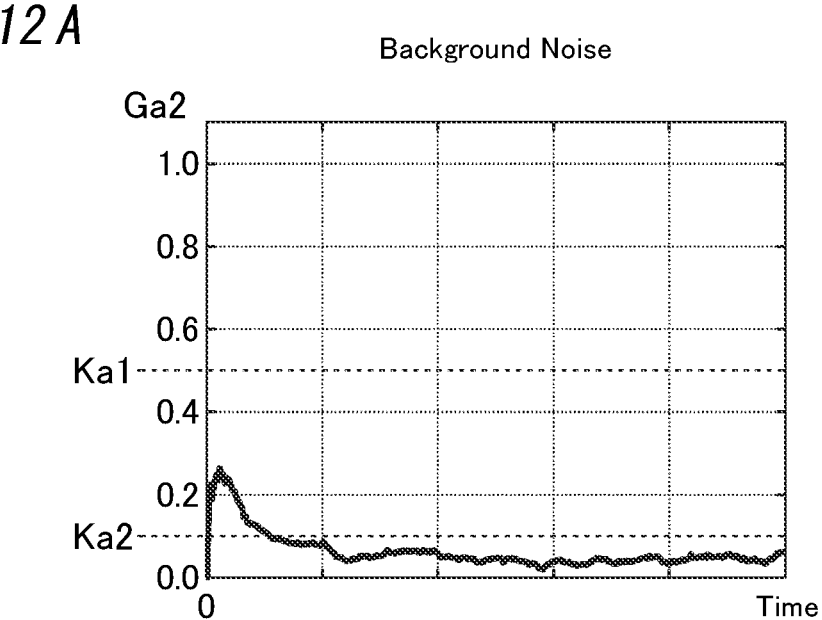
FIGS. 12A and 12B each show how an evaluation value changes with time in the first embodiment.
Figure 12B:
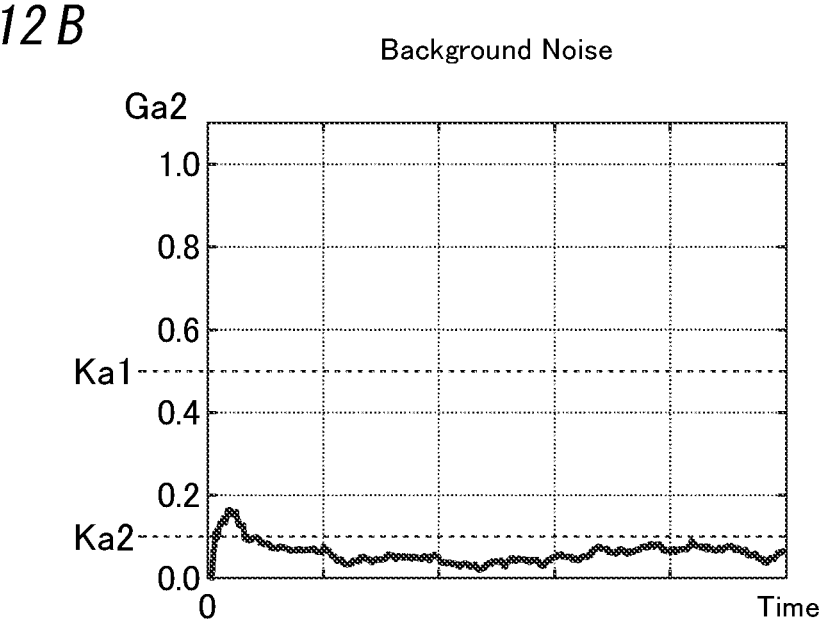

FIGS. 12A and 12B show how the evaluation value Ga2 changes with time in a situation where there are no objects 9 in the irradiation area R1. That is to say, the evaluation value Ga2 is a value representing background noise. In FIGS. 12A and 12B, the evaluation value Ga2 remains less than the evaluation threshold value Ka2 for a longer period of time.

The target determination unit 241 according to this embodiment determines, by comparing the evaluation value Ga2 with two evaluation threshold values Ka1, Ka2, the chances of the object 9 being the target of detection in three stages.

As the decision in the first stage, when finding the evaluation value Ga2 equal to or greater than the evaluation threshold value Ka1, the target determination unit 241 determines that at least a person should be present as the object 9 within the irradiation area R1. That is to say, if the evaluation value Ga2 is equal to or greater than the evaluation threshold value Ka1, then a person should be present as the object 9 within the irradiation area R1. Nevertheless, it is not clear whether there is any disturbance object as the object 9 within the irradiation area R1. Note that when finding that the evaluation value Ga2 remains equal to or greater than the evaluation threshold value Ka1 for a predetermined time or more, the target determination unit 241 preferably determines that at least a person should be present there.

As the decision in the second stage, when finding the evaluation value Ga2 less than the evaluation threshold value Ka1 and equal to or greater than the evaluation threshold value Ka2, the target determination unit 241 determines that at least a disturbance object should be present as the object 9 within the irradiation area R1. That is to say, if the evaluation value Ga2 is less than the evaluation threshold value Ka1 and equal to or greater than the evaluation threshold value Ka2, then a disturbance object should be present as the object 9 within the irradiation area R1. Nevertheless, it is not clear whether there is any person as the object 9 within the irradiation area R1. Note that when finding that the evaluation value Ga2 remains less than the evaluation threshold value Ka1 and equal to or greater than the evaluation threshold value Ka2 for a predetermined time or more, the target determination unit 241 preferably determines that at least a disturbance object should be present there.

As the decision in the third stage, when finding the evaluation value Ga2 less than the evaluation threshold value Ka2, the target determination unit 241 determines that neither a person nor a disturbance object should be present as the object 9 within the irradiation area R1. That is to say, if the evaluation value Ga2 is less than the evaluation threshold value Ka2, then no person or disturbance object should be present as the object 9 within the irradiation area R1. Note that when finding that the evaluation value Ga2 remains less than the evaluation threshold value Ka2 for a predetermined time or more, the target determination unit 241 preferably determines that no person or disturbance object should be present there.

Suppose the body motion signal processing device of Patent Literature 1 cited above is a comparative example. In the comparative example, the amplitude value of a body motion signal component of a reception signal to be detected when no person is present in the irradiation area R1 and the amplitude value of the body motion signal detected when a person is present in the irradiation area R1 are compared with each other to detect the body motion (such as the heart rate or respiratory rate) of the person in the irradiation area R1. According to such a comparative example, in a situation where the evaluation value Ga2 is less than the evaluation threshold value Ka1 and equal to or greater than the evaluation threshold value Ka2, a decision is highly likely to be made that a person should be present in the irradiation area R1.

In contrast, the sensor system A1 and signal processing system 2 according to this embodiment compares the evaluation value Ga2 with the evaluation threshold values Ka1, Ka2, thereby more accurately determining whether the object 9 present in the irradiation area R1 is a person or a disturbance object. That is to say, the sensor system A1 and signal processing system 2 may determine a property of the object 9 accurately enough.

(1.3.3) Signal Processing Method

Figure 13:
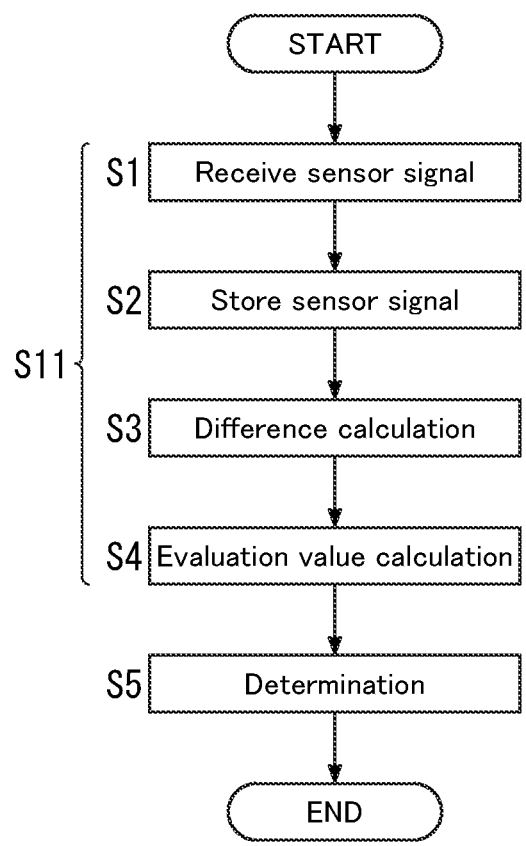
FIG. 13 is a flowchart showing how the signal processing system operates in the first embodiment.

The signal processing method according to this embodiment may be summarized as a flowchart shown in FIG. 13.

The signal processing method shown in FIG. 13 includes a reception step S1, a storage step S2, a difference calculation step S3, an evaluation value calculation step S4, and a determination step S5.

In the reception step S1, the preprocessing unit 21 receives the sensor signal Y0 from the radio wave sensor 1.

In the storage step S2, the storage unit 22 stores, using the sensor signal Y0 that has been amplified and AD converted by the preprocessing unit 21 as a sensor signal Y1, the history of the sensor signals Y1.

In the difference calculation step S3, the difference calculation unit 23 generates, based on the history of the sensor signals Y1 stored in the storage unit 22, a first differential signal $\Delta Y(t0, t1)$ and a second differential signal $\Delta Y(t0, t2)$ as a plurality of differential signals $\Delta Y$. Then, the difference calculation unit 23 obtains the magnitude of the first differential signal $\Delta Y(t0, t1)$ as a first differential value $\Delta Z1$. In addition, the difference calculation unit 23 obtains the magnitude of the second differential signal $\Delta Y(t0, t2)$ as a second differential value $\Delta Z2$.

In the evaluation value calculation step S4, the target determination unit 241 (determination unit 24) obtains the evaluation value Ga by using the $[\Delta Z2/\Delta Z1]$ ratio of the second differential value $\Delta Z2$ to the first differential value $\Delta Z1$.

In the determination step S5, the target determination unit 241 (determination unit 24) determines, using the evaluation value Ga, whether or not the object 9 is a person.

A program stored in a memory of a computer system is preferably designed to cause a processor to perform the signal processing method described above.

The signal processing method and program described above also enable accurately determining whether or not the object 9 is a person as a target of detection.

(1.4) Notification System

The output unit 25 transmits the decision made by the target determination unit 241 to the notification system 3. The notification system 3 notifies, in the form of at least one of an image or a sound, the administrator of the decision made by the target determination unit 241.

Examples of such a notification system 3 include a notification system operated by a business operator who provides the service of watching a designated person as an exemplary object 9. In that case, the person designated as the target of detection may be, for example, an aged person who is a resident of a welfare facility, an aged person who uses a daycare service center, an aged person who lives alone, or an aged person who lives in a residence that provides services for the elderly.

If the state where the person is absent from the irradiation area R1 persists for a predetermined period or more, then the notification system 3 notifies a predetermined terminal device that the person designated as the target of detection is absent. This allows either the administrator or a member of the aged person's family to take an appropriate action when notified of the absence of the person designated as the target of detection.

Note that the person who is the target of detection does not have to be an aged person but may also be, for example, a child who uses a nursery school or a patient who is hospitalized in a health care facility. That is to say, the age, gender, or any other attribute of the person designated as the target of detection are not limited to any particular one.

(1.5) First Variation

In the signal processing system 2 according to the first embodiment described above, if the evaluation value Ga2 is less than the evaluation threshold value Ka1 and equal to or greater than the evaluation threshold value Ka2, then it is not clear whether the person is present or not as the object 9 within the irradiation area R1.

Figure 14:
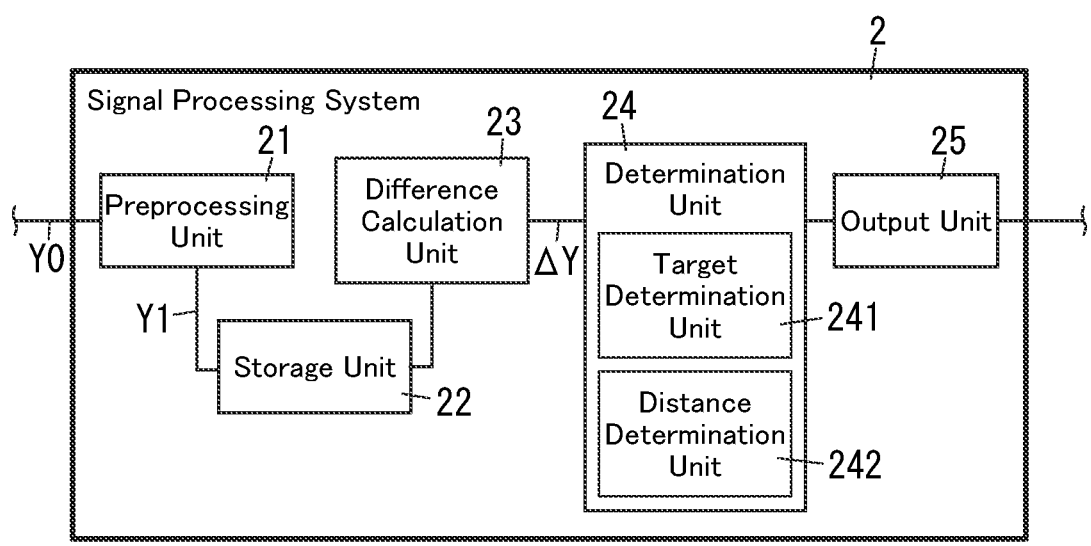
FIG. 14 is a block diagram illustrating a sensor system including a signal processing system according to a first variation of the first embodiment.

Thus, to more accurately determine whether or not the object 9 is the person as the target of detection, the determination unit 24 according to this variation further includes a distance determination unit 242 as shown in FIG. 14. The distance determination unit 242 determines, based on the spectrum (frequency distribution) of a second differential signal $\Delta Y(t0, t2)$, the distance L to the object 9 as a distance determination value. The target determination unit 241 performs determination processing of determining, based on the distance determination value obtained by the distance determination unit 242, whether or not the object 9 is a person.

In addition, the signal processing system 2 sets in advance the directivity of at least one of the transmission antenna 1b or the reception antenna 1c of the radio wave sensor 1 according to the object 9 as the target of detection, thereby limiting the irradiation area R1 of radio waves according to the object 9 as the target of detection. Specifically, the directivity of at least one of the transmission antenna 1b or the reception antenna 1c of the radio wave sensor 1 is set such that the irradiation area R1 includes an area where a person is highly likely to be present but does not include an area where a person is much less likely to be present.

The target determination unit 241 preferably regards some area, where a person is highly likely to be present, out of the irradiation area R1 as a determination area, and determines, based on only the reception wave reflected from the object 9 within the determination area, whether or not the object 9 is a person. That is to say, the target determination unit 241 limits the determination area, thereby reducing the influence of the disturbance object compared to the influence of the person. Consequently, this may reduce the chances of failing to detect the person in the determination area.

Figure 15:
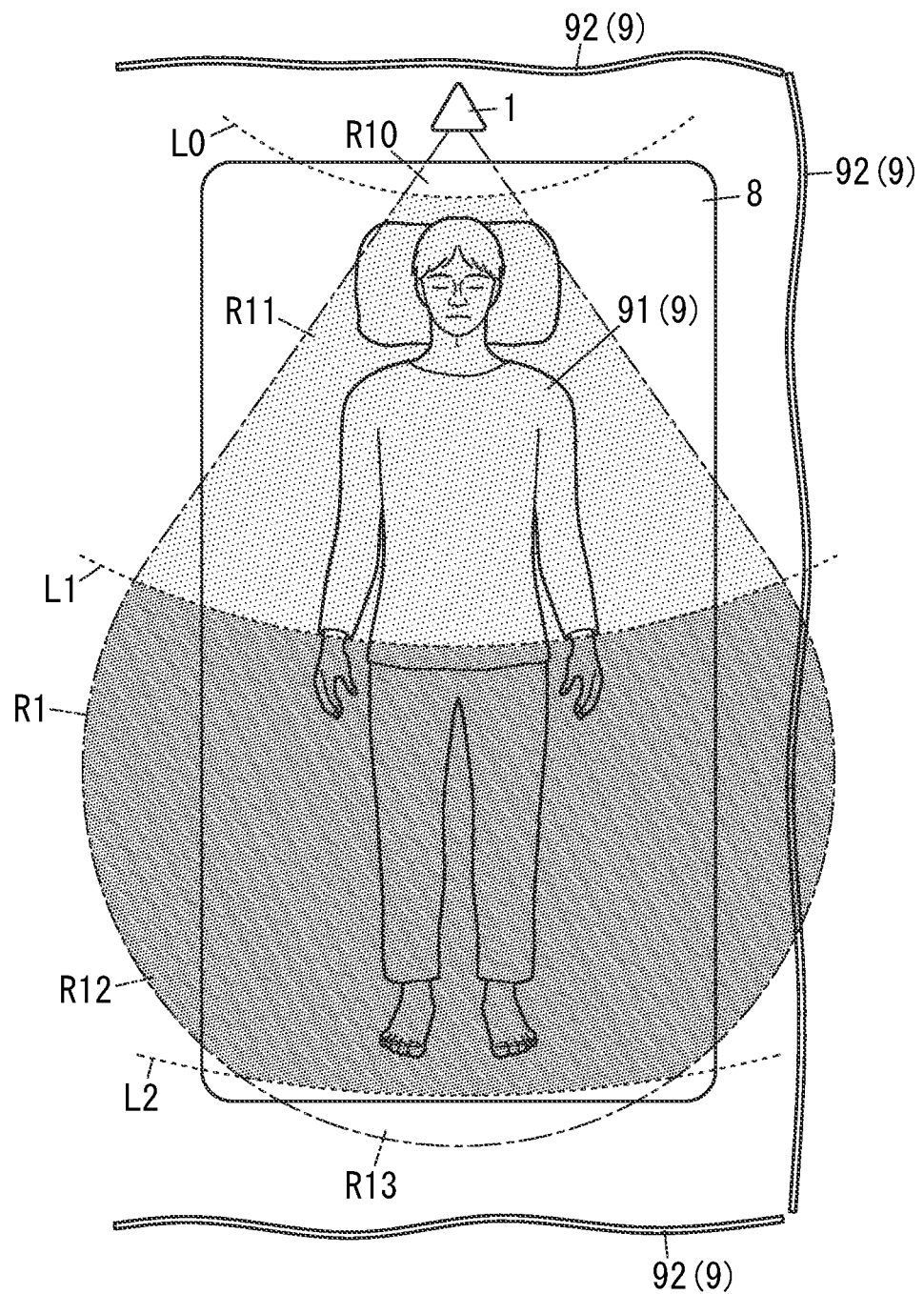
FIG. 15 is a plan view illustrating how determination areas may be set in the first variation of the first embodiment.

FIG. 15 illustrates how the determination area may be set, for example. In this example, a person 91 who is lying in a bed 8 in the shape of a rectangular parallelepiped is supposed to be the object 9 as the target of detection. Curtains 92 are arranged as the objects 9 at both ends along the length (i.e., at both longitudinal ends) of the bed 8 and at one end along the width (i.e., at one latitudinal end) of the bed 8.

In that case, the radio wave sensor 1 is disposed adjacent to the person 91. Specifically, the radio wave sensor 1 may be disposed on, for example, either a headboard of the bed 8 or wall adjacent to the headboard of the bed 8. The directivity of the radio wave sensor 1 is set in a teardrop shape such that the irradiation area R1 as viewed perpendicularly covers the bed 8 as much as possible and covers the curtains 92 as little as possible.

The target determination unit 241 defines an area, where the distance L is less than a distance threshold value L0, out of the irradiation area R1 as a non-determination area R10. In addition, the target determination unit 241 defines an area, where the distance L is equal to or greater than the distance threshold value L0 but less than a distance threshold value L1, of the irradiation area R1 as a determination area R11. Furthermore, the target determination unit 241 defines an area, where the distance L is equal to or greater than the distance threshold value L1 but less than a distance threshold value L2, of the irradiation area R1 as a determination area R12. Furthermore, the target determination unit 241 defines an area, where the distance L is equal to or greater than the distance threshold value L2, of the irradiation area R1 as a non-determination area R13. Note that the distance threshold value L0 is a distance L which is too close to the radio wave sensor 1 to cover the person 91. The distance threshold value L1 is a distance L which covers the upper half of the person's 91 body but hardly covers the lower half of his or her body. The distance threshold value L2 is a value approximately equal to the total length of the bed 8 along the longitudinal axis thereof.

Thus, the determination area R11 is an area which covers the upper half of the body of the person 91 in the bed 8 but does not cover any of the curtains 92 and in which the chances of detecting a disturbance object are slim. The determination area R12 is an area which covers the lower half of the body of the person 91 in the bed 8 and of which one edge is in contact with one of the curtains 92. Nevertheless, the curtain 92 has little influence on the edge of the determination area R12.

When finding the distance determination value obtained by the distance determination unit 242 based on the second differential signal $\Delta Y(t0, t2)$ equal to or greater than the distance threshold value L0 and less than the distance threshold value L2, the target determination unit 241 performs determination processing using the first differential signal $\Delta Y(t0, t1)$ and the second differential signal $\Delta Y(t0, t2)$. Specifically, the target determination unit 241 obtains an evaluation value Ga based on the $[\Delta Z2/\Delta Z1]$ ratio of the second differential value $\Delta Z2$ of the second differential signal $\Delta Y(t0, t2)$ to the first differential value $\Delta Z1$ of the first differential signal $\Delta Y(t0, t1)$ and performs determination processing using the evaluation value Ga. In other words, the target determination unit 241 determines, with respect to only the object 9 present in either of the determination areas R11, R12, whether or not the object 9 is a person. This may reduce the chances of the target determination unit 241 taking a disturbance object such as the curtain 92 for the person 91 by mistake or taking the person 91 for a disturbance object 9 such as the curtain 92 by mistake.

(1.6) Second Variation

Also, in the first embodiment, the target determination unit 241 may determine, by comparing the evaluation value Ga with at least one evaluation threshold value, whether or not the object 9 is the target of detection.

For example, the target determination unit 241 may determine in two stages, by comparing the evaluation value Ga with a single evaluation threshold value, whether the object 9 is the target of detection or not. Alternatively, the target determination unit 241 may determine in four stages, by comparing the evaluation value Ga with three evaluation threshold values, whether the object 9 is the target of detection or not.

(2) Second Embodiment

(2.1) Signal Processing

Figure 16:
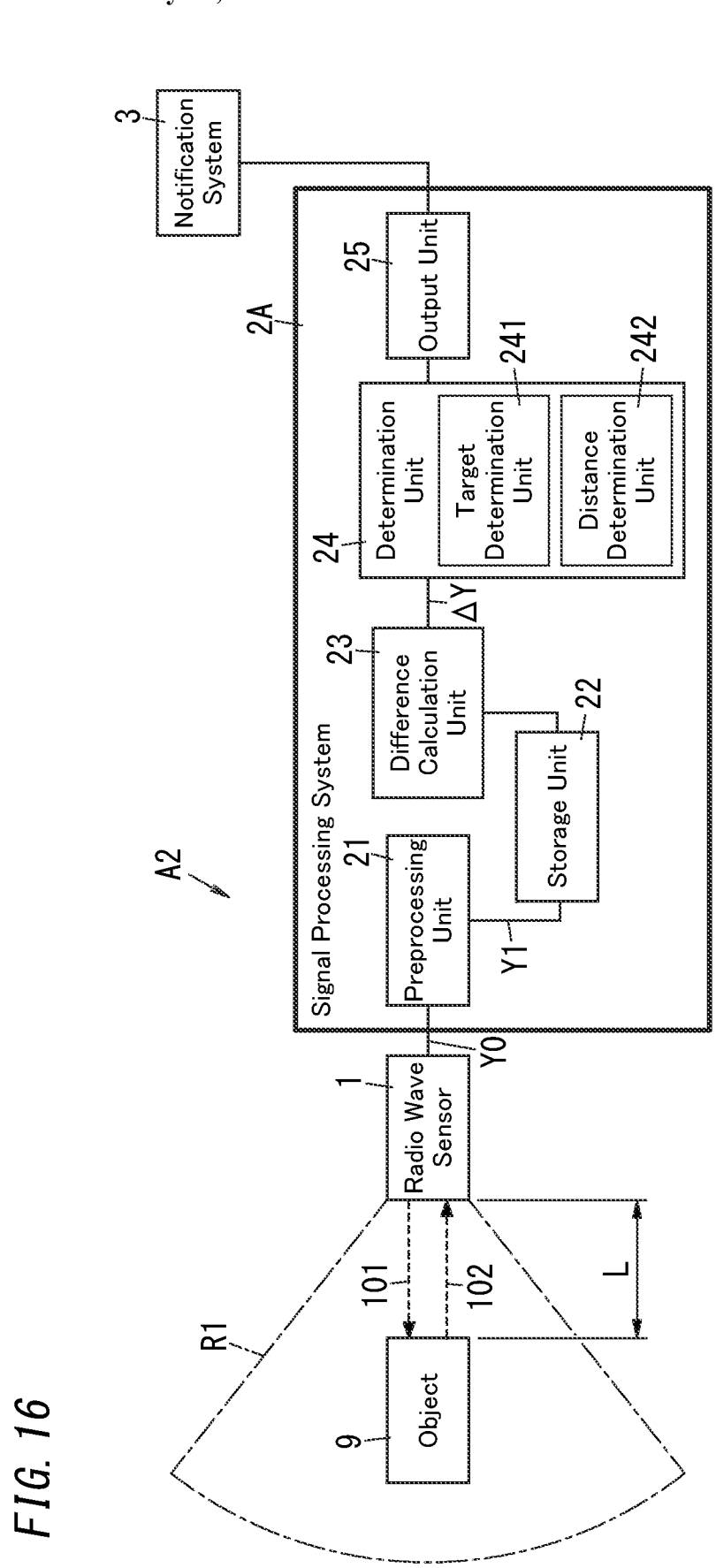
FIG. 16 is a block diagram illustrating a sensor system including a signal processing system according to a second embodiment.

FIG. 16 illustrates a sensor system A2 including a signal processing system 2A according to a second embodiment. In the following description, any constituent element of this second embodiment, having the same function as a counterpart of the first embodiment described above, will be designated by the same reference numeral as that counterpart's, and description thereof will be omitted herein.

Figure 17:
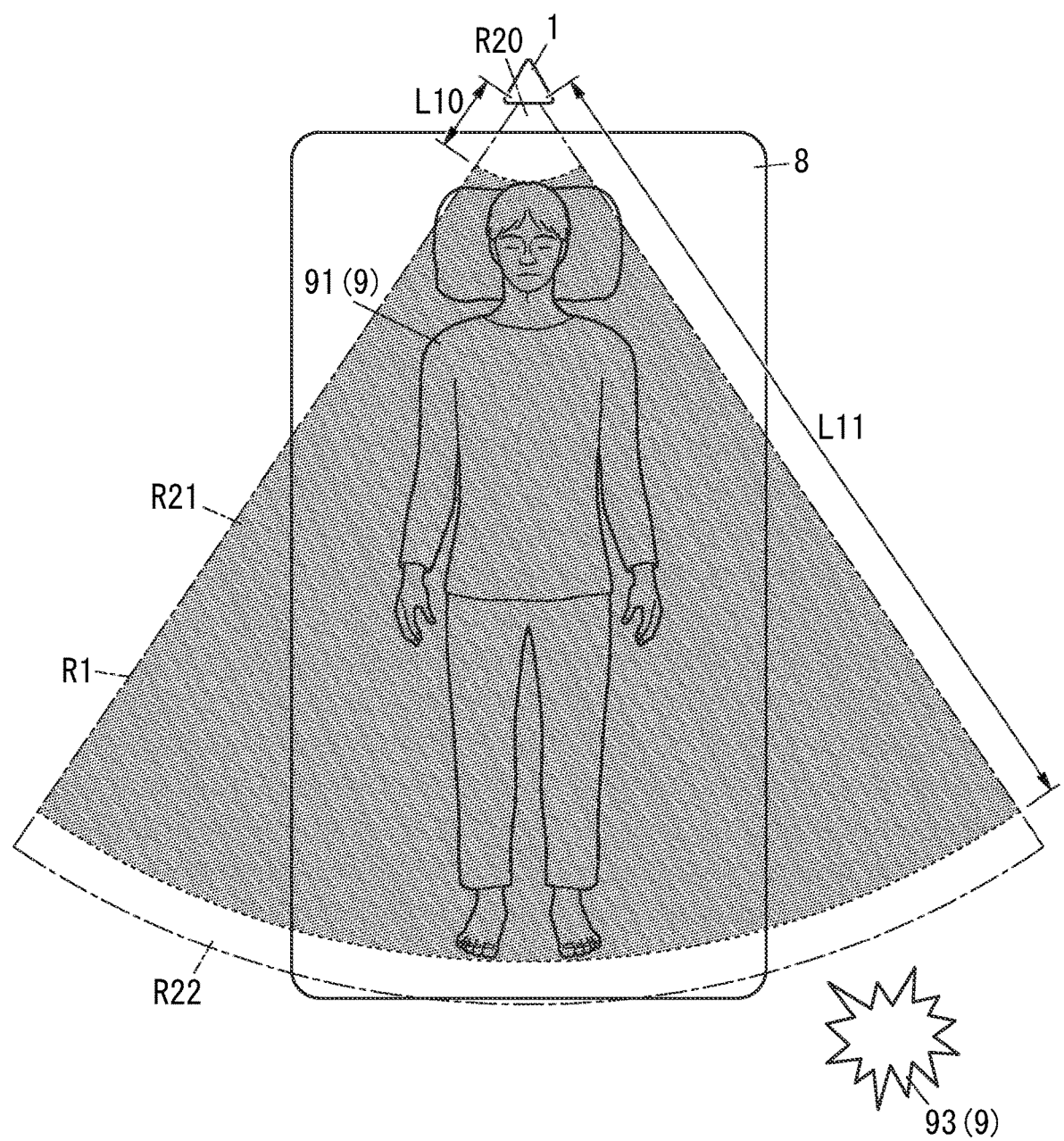
FIG. 17 is a plan view illustrating how a determination area may be set in the second embodiment.

To accurately determine a property of the object 9 as the target of detection, the signal processing system 2A sets the directivity of at least one of the transmission antenna 1b or the reception antenna 1c of the radio wave sensor 1 in advance according to the object 9 as the target of detection, thereby limiting the irradiation area R1 of radio waves according to the object 9 as the target of detection as shown in FIG. 17. Specifically, the directivity of at least one of the transmission antenna 1b or the reception antenna 1c of the radio wave sensor 1 is set such that the irradiation area R1 includes an area where a person 91 is highly likely to be present but does not include an area where a person 91 is much less likely to be present.

In addition, the determination unit 24 of the signal processing system 2A includes a distance determination unit 243 and a target determination unit 244.

The distance determination unit 243 detects, as a peak frequency fp, a frequency at which a peak of signal strength becomes equal to or greater than a peak threshold value Kb1 (see FIG. 18) in a spectrum of the second differential signal ΔY(t0, t2). In addition, the distance determination unit 243 also determines, based on the peak frequency fp, the distance L as a property of the object 9 (i.e., obtains a distance determination value). The distance determination unit 243 generates, as distance data, data about the distance determination value every time the distance determination unit 243 determines the distance L.

Specifically, the distance determination unit 243 converts, as distance measuring preprocessing, the second differential signal ΔY(t0, t2) as a signal in the time domain into a second differential signal ΔY(f) as a signal in the frequency domain by subjecting the second differential signal ΔY(t0, t2) to either FFT or DCT.

Figure 18:
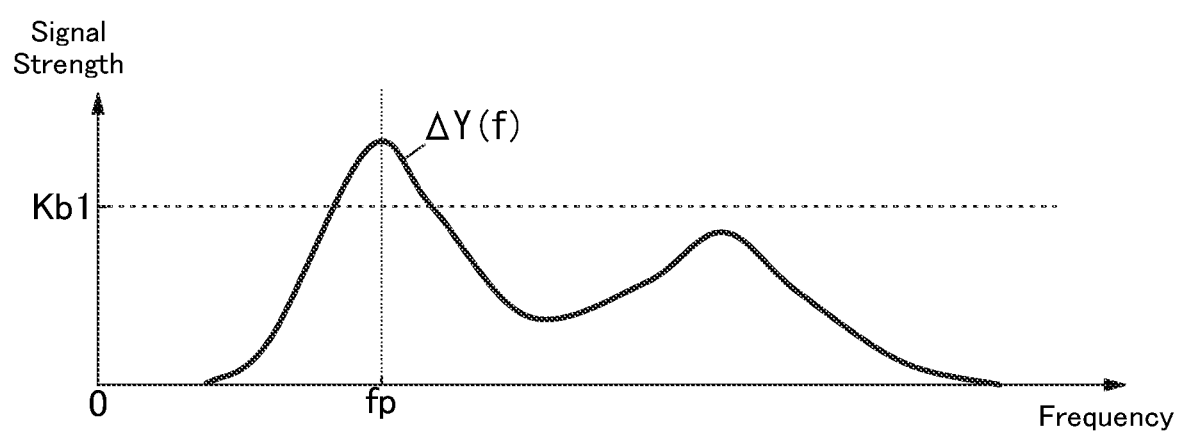
FIG. 18 shows how to perform distance determination processing according to the second embodiment.

FIG. 18 shows an exemplary second differential signal ΔY(f). The distance determination unit 243 compares, as distance determination processing, the signal strength of the second differential signal ΔY(f) with a peak threshold value Kb1. Then, the distance determination unit 243 extracts, as the distance determination processing, a peak frequency fp at which the signal strength of the second differential signal ΔY(f) reaches a peak value in a range equal to or greater than the peak threshold value Kb1. The peak frequency fp corresponds to the beat frequency fb (see Equation (1)). Thus, the distance determination unit 243 may obtain the distance L unequivocally by substituting the peak frequency fp for the beat frequency fb in Equation (1).

Next, the target determination unit 244 defines an area, where a person 91 is highly likely to be present, of the irradiation area R1 as a determination area R21 as shown in FIG. 17. The target determination unit 244 extracts, as reevaluation processing, distance data generated by the reception wave that has been reflected from the object 9 within the determination area R21. That is to say, the target determination unit 244 limits the determination area R21, thereby reducing the influence of the disturbance object 93 compared to the influence of the person 91. Consequently, this may reduce the chances of failing to detect the person 91 in the determination area R21.

Specifically, as shown in FIG. 17, a person 91 who is lying in a bed 8 in the shape of a rectangular parallelepiped is supposed to be the object 9 as the target of detection. In FIG. 17, the radio wave sensor 1 is placed beside the head of the person 91. In addition, a disturbance object 93 is supposed to face the radio wave sensor 1 with the person 91 interposed between the radio wave sensor 1 and the disturbance object 93. In that case, the distance between the radio wave sensor 1 and the disturbance object 93 is longer than the distance between the radio wave sensor 1 and the person 91.

Thus, the target determination unit 244 sets distance threshold values L10, L11 in advance, where the distance threshold values L10, L11 satisfy L10<L11. The target determination unit 244 defines an area, where the distance L is less than the distance threshold value L10, out of the irradiation area R1 as a non-determination area R20. In addition, the target determination unit 244 defines an area, where the distance L is equal to or greater than the distance threshold value L10 but less than a distance threshold value L11, of the irradiation area R1 as a determination area R21. Furthermore, the target determination unit 24 defines an area, where the distance L is equal to or greater than the distance threshold value L11, of the irradiation area R1 as a non-determination area R22. Note that the distance threshold value L10 is a distance L which is too close to the radio wave sensor 1 to cover the person 91. The distance threshold value L11 is a value approximately equal to the total length of the bed 8 along the longitudinal axis thereof.

The target determination unit 244 determines, by comparing the distance determination value with the distance threshold values L10, L11, whether or not the distance determination value is equal to or greater than the distance threshold value L10 and less than the distance threshold value L11.

Figure 19A:
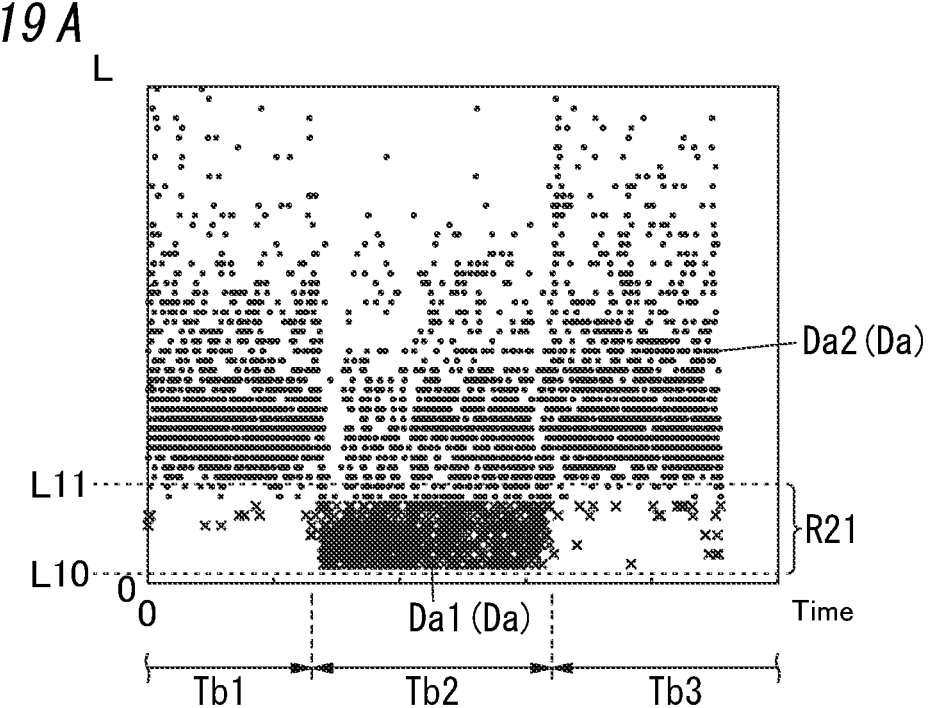
FIG. 19A is a graph plotting a set of distance data according to the second embodiment.

Specifically, FIG. 19A is a graph in which distance data Da, corresponding to a great many distance determination values obtained by the distance determination unit 243 in every computational cycle, are plotted along the time axis. In FIG. 19A, a period Tb1 is a period in which the person 91 is absent from the bed 8. A period Tb2 following the period Tb1 is a period in which the person 91 is lying faceup in the bed 8. A period Tb3 following the period Tb2 is a period in which the person 91 is absent from the bed 8. The distance data Da including the great many distance determination values shown in FIG. 19A includes, in combination, distance data Da1 generated by the person 91 and distance data Da2 generated by the disturbance object. Thus, the target determination unit 244 extracts, from the distance data Da including the great many distance determination values, only the distance data Da, of which the distance determination values are equal to or greater than the distance threshold value L10 and less than the distance threshold value L11, as the distance data Da1 generated by the person 91.

Next, the target determination unit 244 performs index calculation processing by obtaining, using the distance data Da1 thus extracted, an index based on the density per predetermined time of the distance data Da1. The index is a value indicating the likelihood that the object 9 is the person 91. In this embodiment, the larger the index is, the more likely the object 9 is the person 91.

Figure 20:
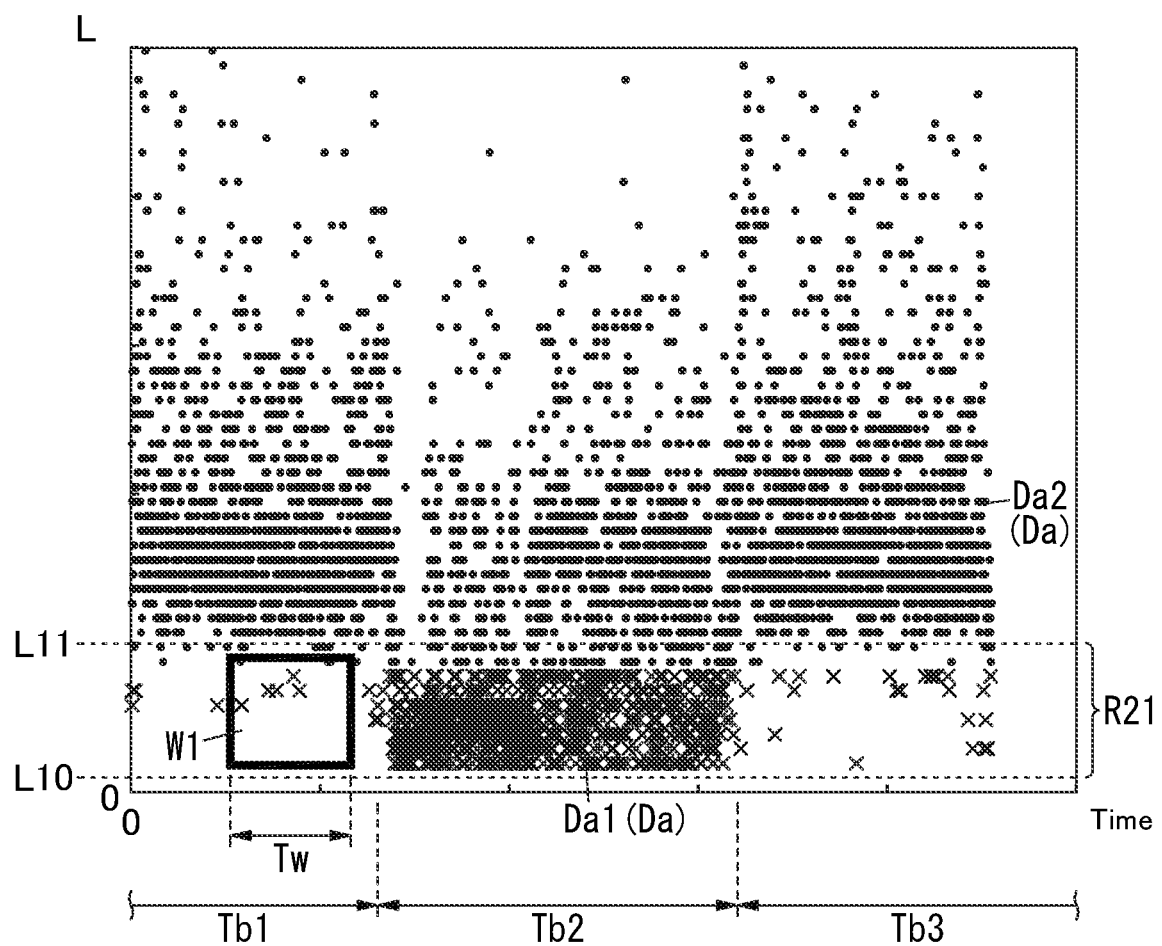
FIG. 20 shows how to perform index calculation processing in the second embodiment.

Specifically, the target determination unit 244 sets an evaluation window W1, of which the time length is a predetermined time Tw, within a range that is equal to or greater than the distance threshold value L10 and less than the distance threshold value L11 as shown in FIG. 20. That is to say, the distance data Da included within the evaluation window W1 is the distance data Da2 and the number of the distance determination values of the distance data Da included within the evaluation window W1 corresponds to the density per predetermined time Tw of the distance data Da2. The target determination unit 244 obtains, as the index, the number of the distance determination values of the distance data Da included within the evaluation window W1 (i.e., the density per predetermined time Tw of the distance data Da2). The target determination unit 244 shifts the evaluation window W1 by predetermined slide time with the passage of time and obtains the index every time the target determination unit 244 shifts the evaluation window W1.

Figure 19B:
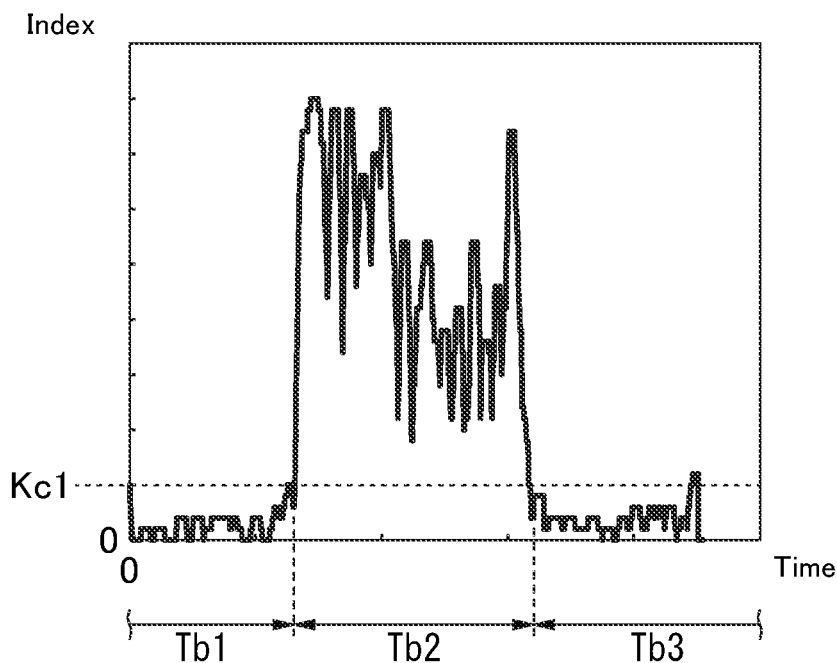
FIG. 19B is a graph showing how an index changes with time in the second embodiment.

FIG. 19B shows the indices obtained based on the distance data Da2 shown in FIG. 19A. The index in the period Tb2 in which the person 91 is lying faceup in the bed 8 is larger than the index in each of the periods Tb1, Tb3 in which the person 91 is absent from the bed 8. Thus, the target determination unit 244 performs the determination processing by comparing the index with a predetermined index threshold value Kc1. When finding that the index remains equal to or greater than the index threshold value Kc1 for a predetermined period or more, the target determination unit 244 determines that the person 91 should be present in the determination area R21.

Figure 21A:
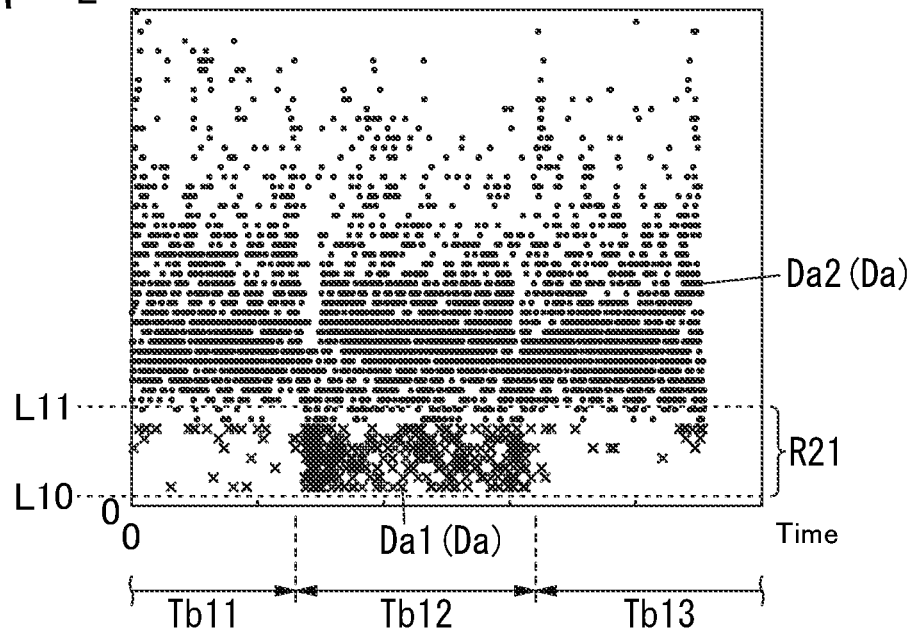
FIG. 21A is a graph plotting another set of distance data according to the second embodiment.
Figure 21B:
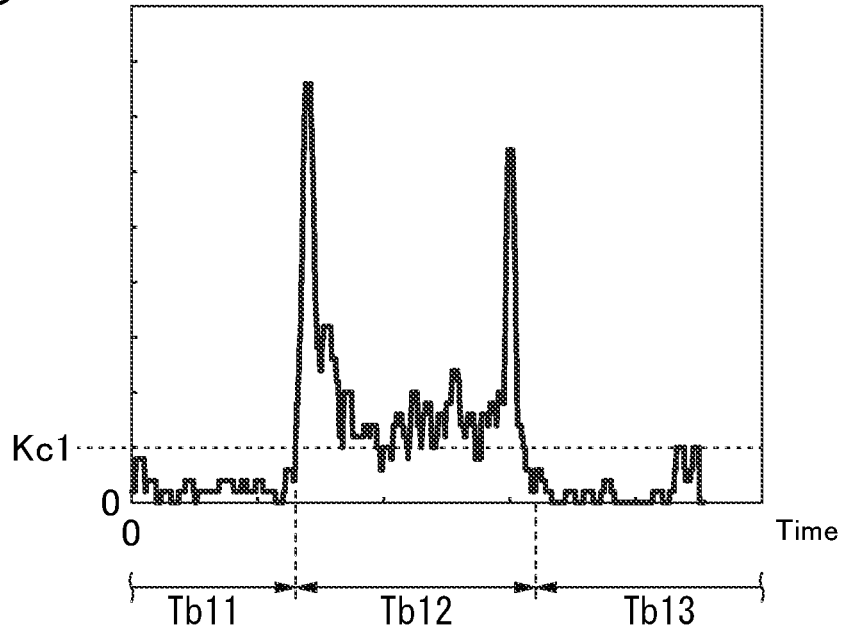
FIG. 21B is a graph showing how another index changes with time in the second embodiment.

FIG. 21A is a graph in which another set of distance data Da are plotted along the time axis. In FIG. 21A, a period Tb11 is a period in which the person 91 is absent from the bed 8. A period Tb12 following the period Tb11 is a period in which the person 91 is lying sideways in the bed 8. A period Tb13 following the period Tb12 is a period in which the person 91 is absent from the bed 8. If the person 91 lies sideways in the bed 8, the chances of the transmission wave 101 (see FIG. 1) sent out from the radio wave sensor 1 being reflected from the back of the person 91 are higher than in a situation where the person 91 is lying faceup in the bed 8. That is to say, this decreases the chances of the person's 91 motion caused by his or her respiration being reflected in the reception wave 102. In this embodiment, however, the index in the period Tb12 in which the person 91 is lying sideways in the bed 8 is larger than the index in any of the periods Tb11, Tb13 in which the person 91 is absent from the bed 8. This allows the target determination unit 244 to determine, by comparing the index with the index threshold value Kc1, that the person 91 should be present in the determination area R21 in the period Tb12.

Figure 22A:
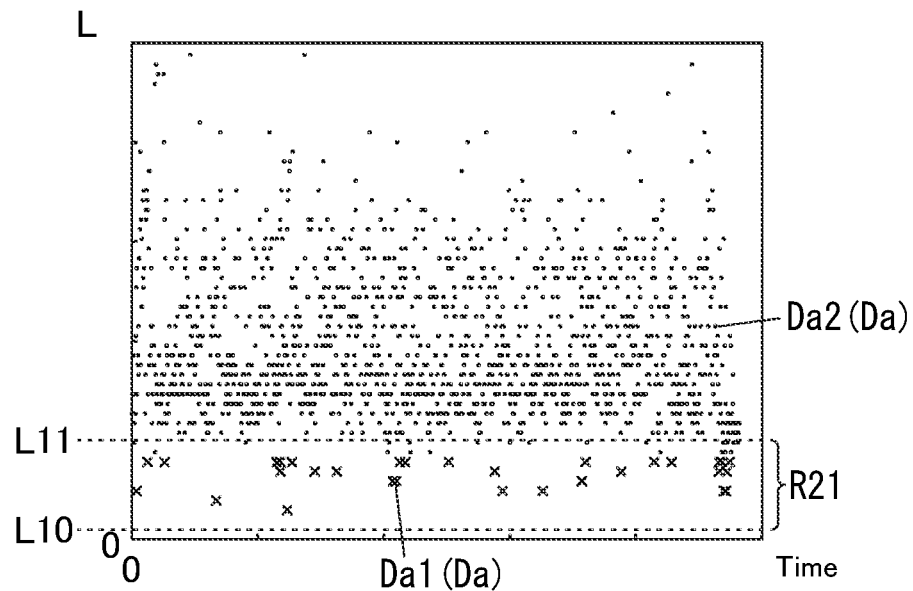
FIG. 22A is a graph plotting still another set of distance data according to the second embodiment.
Figure 22B:
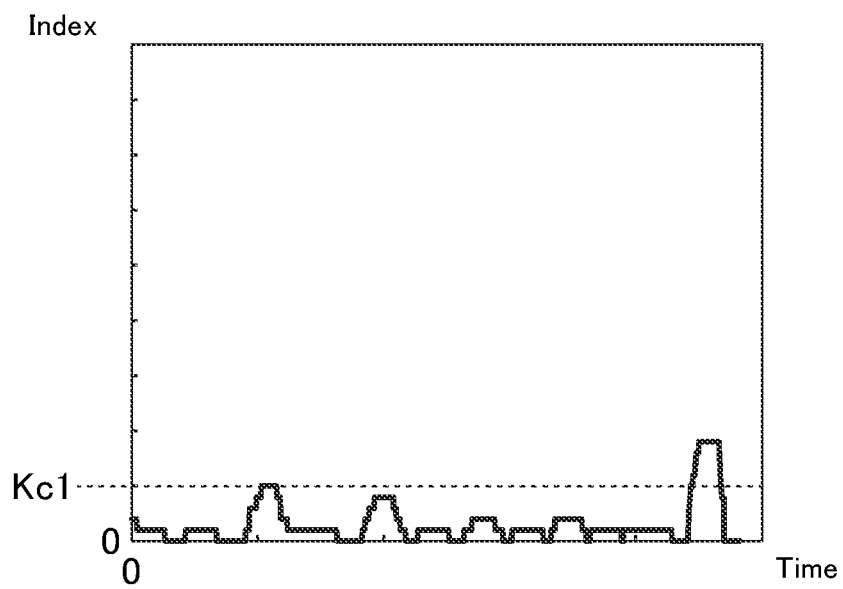
FIG. 22B is a graph showing how still another index changes with time in the second embodiment.

FIG. 22A is a graph in which the distance data Da obtained when only a disturbance object such as the curtain is present in the determination area R21 is plotted along the time axis. In that case, the index becomes smaller than the index threshold value Kc1. This allows the target determination unit 244 to determine, by comparing the index with the index threshold value Kc1, that the person 91 should be absent from the determination area R21.

Figure 23A:
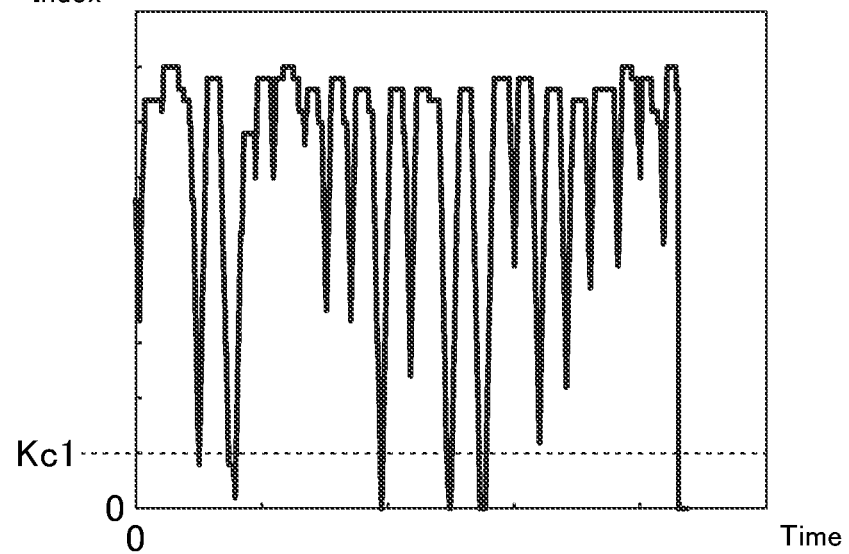
FIGS. 23A and 23B are graphs each showing how yet another index changes with time in the second embodiment.

FIG. 23A shows an index obtained in a situation where the person 91 is lying faceup in the middle of the bed 8. In that case, the index becomes larger than the index threshold value Kc1. This allows the target determination unit 244 to determine, by comparing the index with the index threshold value Kc1, that the person 91 should be present in the determination area R21.

Figure 23B:
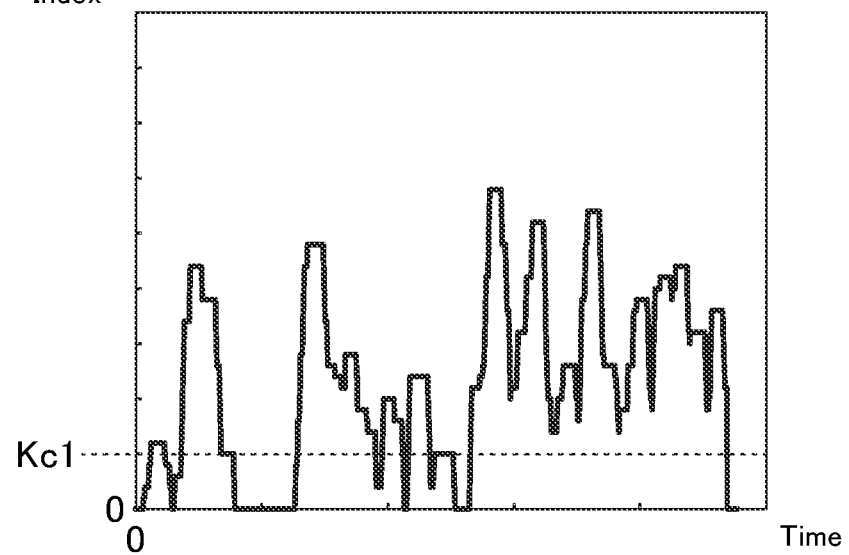

FIG. 23B shows an index obtained in a situation where the person 91 is sitting at an end of the bed 8. In that case, the index becomes larger than the index threshold value Kc1. This allows the target determination unit 244 to determine, by comparing the index with the index threshold value Kc1, that the person 91 should be present in the determination area R21.

Figure 24A:
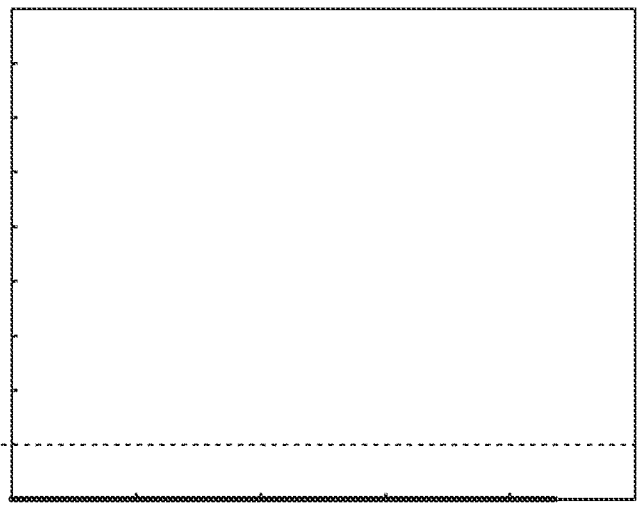
FIGS. 24A, 24B, and 24C are graphs each showing how yet another index changes with time in the second embodiment.

FIG. 24A shows an index obtained in a situation where a curtain is present as the object 9 in the non-determination area R20 (see FIG. 17). In that case, the index becomes smaller than the index threshold value Kc1. This allows the target determination unit 244 to determine, by comparing the index with the index threshold value Kc1, that the person 91 should be absent from the determination area R21.

Figure 24B:
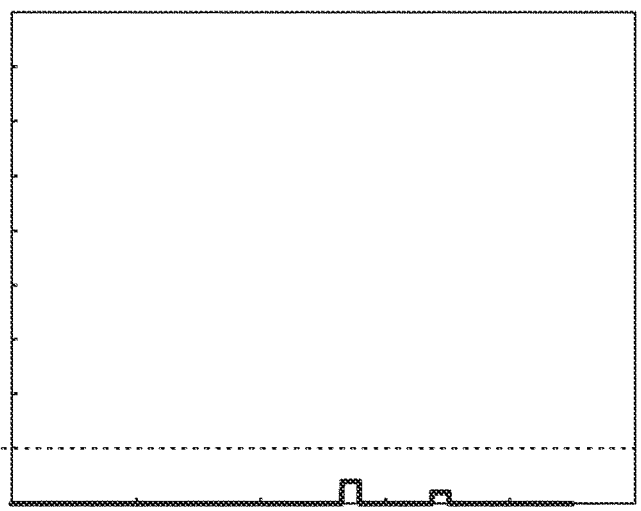

FIG. 24B shows an index obtained in a situation where a curtain is present as the object 9 in the non-determination area R22 (see FIG. 17). In that case, the index becomes smaller than the index threshold value Kc1. This allows the target determination unit 244 to determine, by comparing the index with the index threshold value Kc1, that the person 91 should be absent from the determination area R21.

Figure 24C:
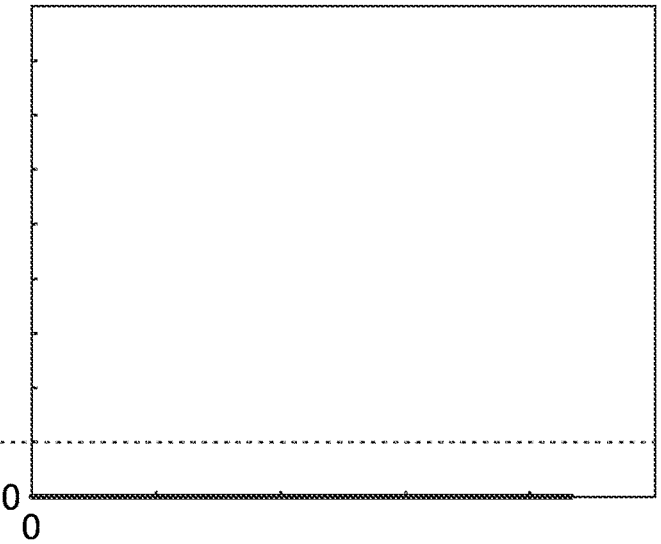

FIG. 24C shows an index obtained in a situation where an electric fan that is swinging is present as the object 9 in the non-determination area R22 (see FIG. 17). In that case, the index becomes smaller than the index threshold value Kc1. This allows the target determination unit 244 to determine, by comparing the index with the index threshold value Kc1, that the person 91 should be absent from the determination area R21.

As can be seen from the foregoing description, the sensor system A2 and signal processing system 2A according to this embodiment may accurately determine, by comparing the index with the index threshold value Kc1, whether or not the object 9 present in the irradiation area R1 is the person 91.

(2.2) Adjustment of Peak Detection Sensitivity

The distance determination unit 243 detects, as a peak frequency fp, a frequency at which a peak of signal strength becomes equal to or greater than the peak threshold value Kb1 (see FIG. 18) in the spectrum of the second differential signal $\Delta Y(t0, t2)$. However, the signal strength of the sensor signal Y1 (Y0) sometimes varies. Thus, if the signal strength of the sensor signal Y1 (Y0) is relatively low, then it is difficult for the distance determination unit 243 to detect the peak frequency fp. That is to say, if the signal strength of the sensor signal Y1 (Y0) is relatively low, then the sensitivity of peak detection by the distance determination unit 243 becomes relatively low, thus making the sensitivity of person detection by the target determination unit 244 relatively low as well.

Thus, the distance determination unit 243 varies, based on the evaluation value Ga, the sensitivity of peak detection by the distance determination unit 243 itself, thereby adjusting the sensitivity of peak detection to allow the sensitivity to fall within a predetermined range. This allows, even if the signal strength of the sensor signal Y1 (Y0) is relatively low, the distance determination unit 243 to detect the peak frequency fp as well. Consequently, the sensor system A2 and the signal processing system 2A may accurately determine the distance L to the object 9. That is to say, the determination unit 24 according to this embodiment may also accurately determine a property of the object 9 by using the evaluation value Ga.

(2.2.1) First Example of Sensitivity Adjustment

For example, the distance determination unit 243 may change, based on the evaluation value Ga1 (see Equation (2)), the peak threshold value Kb1 either continuously or stepwise. In this case, the larger the evaluation value Ga1 is, the more significantly the distance determination unit 243 increases the peak threshold value Kb1. The smaller the evaluation value Ga1 is, the more significantly the distance determination unit 243 decreases the peak threshold value Kb1.

Alternatively, the distance determination unit 243 may also change, based on the evaluation value Ga2 (see Equation (3)), the peak threshold value Kb1 either continuously or stepwise. In this case, the smaller the evaluation value Ga2 is, the more significantly the distance determination unit 243 increases the peak threshold value Kb1. The larger the evaluation value Ga2 is, the more significantly the distance determination unit 243 decreases the peak threshold value Kb1.

The distance determination unit 243 allows, by changing the peak threshold value Kb1, the sensitivity of peak detection to fall within a predetermined range.

(2.2.2) Second Example of Sensitivity Adjustment

For example, the difference calculation unit 23 may amplify each of the sensor signals Y1(t0), Y1(t1), and Y1(t2) at an amplification factor based on the evaluation value Ga1

(see Equation (2)). In this case, the larger the evaluation value Ga1 is, the more significantly the difference calculation unit 23 decreases the amplification factor. The smaller the evaluation value Ga1 is, the more significantly the difference calculation unit 23 increases the amplification factor. That is to say, the difference calculation unit 23 changes, based on the evaluation value Ga1, the respective signal strengths of the sensor signals Y1($t$0), Y1($t$1), and Y1($t$2). Note that the difference calculation unit 23 may set the amplification factor at not only one or more but also less than one.

Alternatively, the difference calculation unit 23 may also amplify each of the sensor signals Y1($t$0), Y1($t$1), and Y1($t$2) at an amplification factor based on the evaluation value Ga2 (see Equation (3)). In this case, the smaller the evaluation value Ga2 is, the more significantly the difference calculation unit 23 decreases the amplification factor. The smaller the evaluation value Ga2 is, the more significantly the difference calculation unit 23 increases the amplification factor. That is to say, the difference calculation unit 23 changes, based on the evaluation value Ga2, the respective signal strengths of the sensor signals Y1($t$0), Y1($t$1), and Y1($t$2). Note that the difference calculation unit 23 may set the amplification factor at not only one or more but also less than one.

The difference calculation unit 23 allows, by changing the respective signal strengths of the sensor signals Y1($t$0), Y1($t$1), and Y1($t$2), the sensitivity of peak detection to fall within a predetermined range.

(2.3) Signal Processing Method

Figure 25:
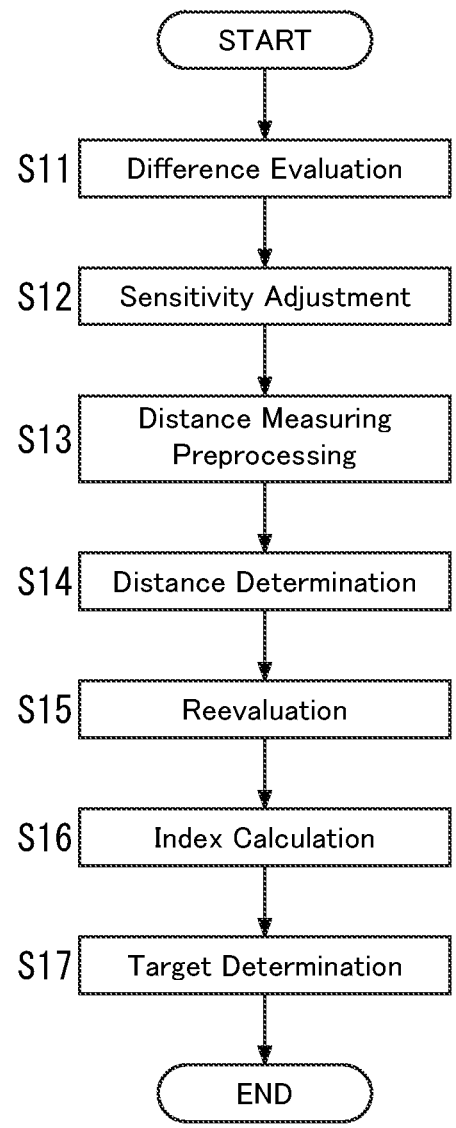
FIG. 25 is a flowchart showing how the signal processing system operates in the second embodiment.

The signal processing method according to this embodiment may be summarized as a flowchart shown in FIG. 25.

The signal processing method shown in FIG. 25 includes a difference evaluation step S11, a sensitivity adjustment step S12, a distance measuring preprocessing step S13, a distance determination step S14, a reevaluation step S15, an index calculation step S16, and a target determination step S17.

The difference evaluation step S11 includes the reception step S1, the storage step S2, the difference calculation step S3, and the evaluation value calculation step S4 according to the first embodiment (see FIG. 13). Specifically, in the difference evaluation step S11, the target determination unit 241 (determination unit 24) obtains the evaluation value Ga by using the [$\Delta Z2/\Delta Z1$] ratio of the second differential value $\Delta Z2$ to the first differential value $\Delta Z1$.

In the sensitivity adjustment step S12, the distance determination unit 243 adjusts the sensitivity of peak detection by changing the peak threshold value Kb1 according to the evaluation value Ga. Alternatively, in the sensitivity adjustment step S12, the difference calculation unit 23 adjusts the sensitivity of peak detection by changing the respective signal strengths of the sensor signals Y1($t$0), Y1($t$1), Y1($t$2) according to the evaluation value Ga.

In the distance measuring preprocessing step S13, the distance determination unit 243 converts the second differential signal $\Delta Y(t0, t2)$ as a signal in the time domain into a second differential signal $\Delta Y(f)$ as a signal in the frequency domain by subjecting the second differential signal $\Delta Y(t0, t2)$ to either FFT or DCT.

In the distance determination step S14, the distance determination unit 243 compares the signal strength of the second differential signal $\Delta Y(f)$ with a peak threshold value Kb1, thereby extracting a peak frequency fp at which the signal strength of the second differential signal $\Delta Y(f)$ reaches a peak value in a range equal to or greater than the peak threshold value Kb1.

In the reevaluation step S15, the target determination unit 244 extracts distance data Da1 generated by the reception wave that has been reflected from the object 9 within the determination area R21 (see FIG. 17) in the irradiation area R1.

In the index calculation step S16, the target determination unit 244 obtains, using the distance data Da1 extracted, an index based on the density per predetermined time of the distance data Da1.

In the target determination step S17, the target determination unit 244 compares the index with a predetermined index threshold value Kc1. When finding that the index remains equal to or greater than the index threshold value Kc1 for a predetermined time or more, the target determination unit 244 determines that a person 91 should be present in the determination area R21.

A program stored in a memory of a computer system is preferably designed to cause a processor to perform the signal processing method described above.

The signal processing method and program described above also enable accurately determining a property of the object 9.

(3) Other Variations

The signal processing system described above obtains the evaluation value Ga by using the respective differential values (namely, the first differential value $\Delta Z1$ and the second differential value $\Delta Z2$) of the two differential signals (namely, the first differential signal $\Delta Y(t0, t1)$ and the second differential signal $\Delta Y(t0, t2)$). However, the signal processing system may obtain the evaluation value Ga by using respective differential values of three or more differential signals.

Alternatively, the ratio $\Delta Z1/\Delta Z2$ of the first differential value $\Delta Z1$ to the second differential value $\Delta Z2$ may be used instead of the $\Delta Z2/\Delta Z1$ ratio described above.

Also, the object 9 as the target of detection does not have to be a person 91 but may also be an animal such as a dog or a cat, a robot, a machine having a moving part, a movable machine, an electrical device having a moving part, or a movable electrical device, for example.

Optionally, the signal processing system may also use, as the differential signal, the difference between the sensor signal Y0 in a situation where the object 9 is the person 91 as the target of detection and the sensor signal Y0 in a situation where the object 9 is the disturbance object 93. That is to say, the signal processing system may also achieve the same advantages as the above-described ones by using the differential signal between a plurality of sensor signals Y0 with respect to mutually different objects 9, instead of using the differential signal between a plurality of sensor signals Y0 that are shifted from each other along the time axis.

Furthermore, the radio wave sensor 1 does not have to be the FMCW radio wave sensor as long as the radio wave sensor 1 may measure the distance to the object 9. Alternatively, the radio wave sensor 1 may be a binary frequency shift keying (FSK) radio wave sensor as well.

Optionally, the embodiments and their variations described above may be adopted in combination as appropriate.

(4) Recapitulation

A signal processing system (2, 2A) according to a first aspect of the exemplary embodiment receives, from a radio wave sensor (1), a sensor signal (Y0) including information about a distance (L) between the radio wave sensor (1) and an object (9). The radio wave sensor (1) sends out a radio wave as a transmission wave (101) and receives, as a reception wave (102), the radio wave reflected from the object (9). The signal processing system (2, 2A) includes a difference calculation unit (23) and a determination unit (24). The difference calculation unit (23) uses a sensor signal (Y1(*t*0)) at a reference timing (t0) and a plurality of the sensor signals (Y1(*t*1), Y1(*t*2)) at a plurality of comparative timings (t1, t2) shifted from the reference timing (t0). The difference calculation unit (23) generates a plurality of differential signals (ΔY(t0, t1), ΔY(t0, t2)) as respective differences between the sensor signal (Y1(*t*0)) at the reference timing (t0) and the plurality of the sensor signals (Y1(*t*1), Y1(*t*2)) at the plurality of comparative timings (t1, t2) and obtains respective magnitudes of the plurality of differential signals (ΔY(t0, t1), ΔY(t0, t2)) as a plurality of differential values (ΔZ, ΔZ1, ΔZ2). The determination unit (24) obtains an evaluation value (Ga, Ga1, Ga2) based on the plurality of differential values (ΔZ, ΔZ1, ΔZ2) and determines a property of the object (9) by using the evaluation value (Ga, Ga1, Ga2).

A signal processing system (2, 2A) having such a configuration may accurately determine a property of the object (9).

In a signal processing system (2, 2A) according to a second aspect of the exemplary embodiment, which may be implemented in conjunction with the first aspect, each of the plurality of comparative timings (t1, t2) is preferably earlier than the reference timing (t0).

A signal processing system (2, 2A) having such a configuration may accurately determine a property of the object (9).

In a signal processing system (2, 2A) according to a third aspect of the exemplary embodiment, which may be implemented in conjunction with the first or second aspect, each of the plurality of differential values (ΔZ, ΔZ1, ΔZ2) is preferably an average value, an effective value (RMS value), or a standard deviation of the respective magnitudes of the plurality of differential signals (ΔY(t0, t1), ΔY(t0, t2)).

A signal processing system (2, 2A) having such a configuration may obtain the respective magnitudes of the plurality of differential signals (ΔY(t0, t1), ΔY(t0, t2)) as specific values.

In a signal processing system (2, 2A) according to a fourth aspect of the exemplary embodiment, which may be implemented in conjunction with any one of the first to third aspects, the determination unit (24) preferably uses, as the evaluation value (Ga, Ga1, Ga2), a ratio (ΔZ2/ΔZ1, ΔZ1/ΔZ2) of the plurality of differential values (ΔZ1, ΔZ2).

A signal processing system (2, 2A) having such a configuration may obtain the evaluation value (Ga, Ga1, Ga2) as a relative value, thus improving the accuracy of determination processing.

In a signal processing system (2) according to a fifth aspect of the exemplary embodiment, which may be implemented in conjunction with any one of the first to fourth aspects, the determination unit (24) preferably includes a target determination unit (241). The target determination unit (241) uses the evaluation value (Ga, Ga1, Ga2) to determine, as the property of the object (9), whether or not the object (9) is a predetermined target of detection (91).

A signal processing system (2) having such a configuration may determine, by using the evaluation value (Ga, Ga1, Ga2) directly, whether or not the object (9) is the target of detection (91).

In a signal processing system (2) according to a sixth aspect of the exemplary embodiment, which may be implemented in conjunction with the fifth aspect, the target determination unit (241) preferably determines, by comparing the evaluation value (Ga, Ga1, Ga2) with at least one evaluation threshold value (Ka1, Ka2), whether or not the object (9) is the predetermined target of detection (91).

A signal processing system (2) having such a configuration may determine, by using the evaluation value (Ga, Ga1, Ga2) directly, whether or not the object (9) is the target of detection (91).

In a signal processing system (2) according to a seventh aspect of the exemplary embodiment, which may be implemented in conjunction with the sixth aspect, the at least one evaluation threshold value (Ka1, Ka2) includes a plurality of evaluation threshold values (Ka1, Ka2). The target determination unit (241) preferably determines, by comparing the evaluation value (Ga, Ga1, Ga2) with two of the plurality of evaluation threshold values (Ka1, Ka2), the chances of the object (9) being the target of detection (91) in three stages.

A signal processing system (2) having such a configuration may determine, by using the evaluation value (Ga, Ga1, Ga2) directly, the chances of the object (9) being the target of detection (91) in three stages.

In a signal processing system (2A) according to an eighth aspect of the exemplary embodiment, which may be implemented in conjunction with any one of the first to fourth aspects, the sensor signal (Y0) is preferably a signal, of which a frequency varies according to the distance (L). The determination unit (24) preferably includes a distance determination unit (243). The distance determination unit (243) preferably detects, as a peak frequency (fp), a frequency at which a peak of signal strength becomes equal to or greater than a peak threshold value (Kb1) in a spectrum of at least one of the plurality of differential signals (ΔY(t0, t1), ΔY(t0, t2)) and determines, based on the peak frequency (fp), the distance (L) as the property of the object (9). The distance determination unit (243) changes the peak threshold value (Kb1) according to the evaluation value (Ga, Ga1, Ga2).

A signal processing system (2A) having such a configuration may accurately determine the distance (L) to the object (9).

In a signal processing system (2A) according to a ninth aspect of the exemplary embodiment, which may be implemented in conjunction with any one of the first to fourth aspects, the sensor signal (Y0) is preferably a signal, of which a frequency varies according to the distance (L). The determination unit (24) preferably includes a distance determination unit (243). The distance determination unit (243) detects, as a peak frequency (fp), a frequency at which a peak of signal strength becomes equal to or greater than a peak threshold value (Kb1) in a spectrum of at least one of the plurality of differential signals (ΔY(t0, t1), ΔY(t0, t2)) and determines, based on the peak frequency (fp), the distance (L) as the property of the object (9). The difference calculation unit (23) changes, based on the evaluation value (Ga, Ga1, Ga2), signal strength of the sensor signal (Y1(*t*0)) at the reference timing (t0) and signal strengths of the plurality of sensor signals (Y1(*t*1), Y1(*t*2)) at the plurality of comparative timings (t1, t2).

A signal processing system (2A) having such a configuration may accurately determine the distance (L) to the object (9).

In a signal processing system (2A) according to a tenth aspect of the exemplary embodiment, which may be implemented in conjunction with the eighth or ninth aspect, the determination unit (24) preferably further includes a target determination unit (244) to determine, as the property of the object (9), whether or not the object (9) is a predetermined target of detection (91). The distance determination unit (243) generates distance data (Da) every time the distance determination unit (243) determines the distance (L). The target determination unit (244) determines, by obtaining an index based on a density per predetermined time (Tw) of the distance data (Da) and comparing the index with an index threshold value (Kc1), whether or not the object (9) is the predetermined target of detection (91).

A signal processing system (2A) having such a configuration may accurately determine whether or not the object (9) is the target of detection (91).

In a signal processing system (2, 2A) according to an eleventh aspect of the exemplary embodiment, which may be implemented in conjunction with the fifth, sixth, seventh, or tenth aspect, the target determination unit (241, 244) preferably determines, with respect to only the object (9), to which the distance (L) from the radio wave sensor (1) falls within a predetermined range, whether or not the object (9) is the predetermined target of detection (91).

A signal processing system (2, 2A) having such a configuration may accurately determine, by reducing the influence of a disturbance object (93), whether or not the object (9) is the target of detection (91).

In a signal processing system (2, 2A) according to a twelfth aspect of the exemplary embodiment, which may be implemented in conjunction with any one of the first to eleventh aspects, the difference calculation unit (23) preferably sets two of the plurality of comparative timings as two comparative timings (t1, t2). The difference calculation unit (23) generates two differential signals ($\Delta Y(t0, t1)$, $\Delta Y(t0, t2)$) as respective differences between the sensor signal (Y1($t0$)) at the reference timing (t0) and two of the plurality of the sensor signals (Y1($t1$), Y1($t2$)) at the two comparative timings (t1, t2). Then, the difference calculation unit (23) obtains respective magnitudes of the two differential signals ($\Delta Y(t0, t1)$, $\Delta Y(t0, t2)$) as two differential values ($\Delta Z1$, $\Delta Z2$).

A signal processing system (2, 2A) having such a configuration may accurately determine the property of the object (9).

In a signal processing system (2, 2A) according to a thirteenth aspect of the exemplary embodiment, which may be implemented in conjunction with the twelfth aspect, the two comparative timings (t1, t2) are preferably a first comparative timing (a) and a second comparative timing (t2). The first comparative timing (a) is closer to the reference timing (t0) than the second comparative timing (t2) is. A time length between the reference timing (t0) and the second comparative timing (t2) is equal to or greater than a quarter of one respiratory cycle of a person.

A signal processing system (2, 2A) having such a configuration may accurately determine a property of a person (91) as the target of detection.

A sensor system (A1, A2) according to a fourteenth aspect of the exemplary embodiment includes the signal processing system (2, 2A) according to any one of the first to thirteenth aspects and the radio wave sensor (1).

A sensor system (A1, A2) having such a configuration may accurately determine a property of the object (9).

In a sensor system (A1, A2) according to a fifteenth aspect of the exemplary embodiment, which may be implemented in conjunction with the fourteenth aspect, the radio wave sensor (1) includes: a transmission antenna (1b) to send out the transmission wave (101); and a reception antenna (1c) to receive the reception wave (102). At least one of the transmission antenna (1b) or the reception antenna (1c) preferably has directivity.

A sensor system (A1, A2) having such a configuration may accurately determine a property of the object (9) by reducing the influence of a disturbance object (93).

A signal processing method according to a sixteenth aspect of the exemplary embodiment includes receiving, from a radio wave sensor (1), a sensor signal (Y0) including information about a distance (L) between the radio wave sensor (1) and an object (9). The radio wave sensor (1) sends out a radio wave as a transmission wave (101) and receives, as a reception wave (102), the radio wave reflected from the object (9). The signal processing method includes a difference calculation step (S3) and a determination step (S5, S14). The difference calculation step (S3) includes using the sensor signal (Y1($t0$)) at a reference timing (t0) and a plurality of the sensor signals (Y1($t1$), Y1($t2$)) at a plurality of comparative timings (t1, t2) shifted from the reference timing (t0). The difference calculation step (S3) includes generating a plurality of differential signals ($\Delta Y(t0, t1)$, $\Delta Y(t0, t2)$) as respective differences between the sensor signal (Y1($t0$)) at the reference timing (t0) and the plurality of the sensor signals (Y1($t1$), Y1($t2$)) at the plurality of comparative timings (t1, t2) and obtaining respective magnitudes of the plurality of differential signals ($\Delta Y(t0, t1)$, $\Delta Y(t0, t2)$) as a plurality of differential values ($\Delta Z$, $\Delta Z1$, $\Delta Z2$). The determination step (S5, S14) includes obtaining an evaluation value (Ga, Ga1, Ga2) based on the plurality of differential values ($\Delta Z$, $\Delta Z1$, $\Delta Z2$) and determining a property of the object (9) by using the evaluation value (Ga, Ga1, Ga2).

This signal processing method enables accurately determining a property of the object (9).

A program according to a seventeenth aspect of the exemplary embodiment is designed to cause a computer system to perform the signal processing method according to the sixteenth aspect.

This program enables accurately determining a property of the object (9).

REFERENCE SIGNS LIST

1 Radio Wave Sensor
1b Transmission Antenna
1c Reception Antenna
101 Transmission Wave
102 Reception Wave
2, 2A Signal Processing System
23 Difference Calculation Unit
24 Determination Unit
243 Distance Determination Unit
244 Target Determination Unit
9 Object
91 Person (Target of Detection)
L Distance
Y0, Y1($t0$), Y1($t1$), Y1($t2$) Sensor Signal
t0 Reference Timing
t1 First Comparative Timing (Comparative Timing)
t2 Second Comparative Timing (Comparative Timing)
$\Delta Y(t0, t1)$, $\Delta Y(t0, t2)$ Differential Signal
$\Delta Z$, $\Delta Z1$, $\Delta Z2$ Differential Value
Ga, Ga1, Ga2 Evaluation Value
Ka1, Ka2 Evaluation Threshold Value
Kb1 Peak Threshold Value
Kc1 Index Threshold Value
fp Peak Frequency Da Distance Data
Tw Predetermined Time
S3 Difference Calculation Step
S5 Determination Step
S14 Distance Determination Step (Determination Step)

The invention claimed is:

1. A signal processing system configured to receive a plurality of sensor signals from a radio wave sensor, the radio wave sensor being configured to send out a radio wave as a transmission wave and receive, as a reception wave, the radio wave reflected from an object, each of the plurality of sensor signals including information about a distance between the radio wave sensor and the object, the signal processing system comprising:
a difference calculation unit configured to use one of the plurality of sensor signals at a reference timing as a reference sensor signal and other sensor signals of the plurality of sensor signals at a plurality of comparative timings shifted from the reference timing as comparative sensor signals, to generate a plurality of differential signals as respective differences between the reference sensor signal at the reference timing and the comparative sensor signals at the plurality of comparative timings and to obtain respective magnitudes of the plurality of differential signals as a plurality of differential values; and
a determination unit configured to obtain an evaluation value based on the plurality of differential values and determine a property of the object by using the evaluation value.

2. The signal processing system of claim 1, wherein each of the plurality of comparative timings is earlier than the reference timing.

3. The signal processing system of claim 1, wherein each of the plurality of differential values is an average value, an effective value, or a standard deviation of the respective magnitudes of the plurality of differential signals.

4. The signal processing system of claim 1, wherein the determination unit is configured to use, as the evaluation value, a ratio of the plurality of differential values.

5. The signal processing system of claim 1, wherein the determination unit includes a target determination unit configured to use the evaluation value to determine, as the property of the object, whether or not the object is a predetermined target of detection.

6. The signal processing system of claim 5, wherein the target determination unit is configured to determine, by comparing the evaluation value with at least one evaluation threshold value, whether or not the object is the predetermined target of detection.

7. The signal processing system of claim 6, wherein the at least one evaluation threshold value includes a plurality of evaluation threshold values, and
the target determination unit is configured to determine, by comparing the evaluation value with two of the plurality of evaluation threshold values, the chances of the object being the target of detection in three stages.

8. The signal processing system of claim 5, wherein the target determination unit is configured to determine, with respect to only the object, to which the distance from the radio wave sensor falls within a predetermined range, whether or not the object is the predetermined target of detection.

9. The signal processing system of claim 1, wherein each of the plurality of sensor signals is a signal, of which a frequency varies according to the distance,
the determination unit includes a distance determination unit configured to detect, as a peak frequency, a frequency at which a peak of signal strength becomes equal to or greater than a peak threshold value in a spectrum of at least one of the plurality of differential signals and determine, based on the peak frequency, the distance as the property of the object, and
the distance determination unit is configured to change the peak threshold value according to the evaluation value.

10. The signal processing system of claim 9, wherein the determination unit further includes a target determination unit configured to determine, as the property of the object, whether or not the object is a predetermined target of detection,
the distance determination unit is configured to generate distance data every time the distance determination unit determines the distance, and
the target determination unit is configured to determine, by obtaining an index based on a density per predetermined time of the distance data and comparing the index with an index threshold value, whether or not the object is the predetermined target of detection.

11. The signal processing system of claim 1, wherein each of the plurality of sensor signals is a signal, of which a frequency varies according to the distance,
the determination unit includes a distance determination unit configured to detect, as a peak frequency, a frequency at which a peak of signal strength becomes equal to or greater than a peak threshold value in a spectrum of at least one of the plurality of differential signals and determine, based on the peak frequency, the distance as the property of the object, and
the difference calculation unit is configured to change, based on the evaluation value, signal strength of the reference sensor signal at the reference timing and signal strengths of the comparative sensor signals at the plurality of comparative timings.

12. The signal processing system of claim 1, wherein the difference calculation unit is configured to set two of the plurality of comparative timings as two comparative timings, generate two differential signals as respective differences between the reference sensor signal at the reference timing and two of the comparative sensor signals at the two comparative timings, and obtain respective magnitudes of the two differential signals as two differential values.

13. The signal processing system of claim 12, wherein the two comparative timings are a first comparative timing and a second comparative timing,
the first comparative timing is closer to the reference timing than the second comparative timing is, and
a time length between the reference timing and the second comparative timing is equal to or greater than a quarter of one respiratory cycle of a person.

14. A sensor system comprising:
the signal processing system of claim 1, and
the radio wave sensor.

15. The sensor system of claim 14, wherein the radio wave sensor includes: a transmission antenna configured to send out the transmission wave; and a reception antenna configured to receive the reception wave, and
at least one of the transmission antenna or the reception antenna has directivity.

16. A signal processing method comprising receiving a plurality of sensor signals from a radio wave sensor, the radio wave sensor being configured to send out a radio wave as a transmission wave and receive, as a reception wave, the radio wave reflected from an object, each of the plurality of sensor signals including information about a distance between the radio wave sensor and the object, the signal processing method comprising:

a difference calculation step including using one of the plurality of sensor signals at a reference timing as a reference sensor signal and others of the plurality of sensor signals at a plurality of comparative timings shifted from the reference timing as comparative sensor signals, to generate a plurality of differential signals as respective differences between the reference sensor signal at the reference timing and the comparative sensor signals at the plurality of comparative timings and obtaining respective magnitudes of the plurality of differential signals as a plurality of differential values; and a determination step including obtaining an evaluation value based on the plurality of differential values and determining a property of the object by using the evaluation value.

17. A non-transitory storage medium storing a program that is designed to cause a computer system to perform the signal processing method of claim 16.

* * * * *